(12) United States Patent
Huang et al.

(10) Patent No.: US 7,105,289 B2
(45) Date of Patent: Sep. 12, 2006

(54) INVERSE EMULSION METHODS OF MAKING POLYMERIC IMPRINT BEADS

(75) Inventors: Chin-Shiou Huang, San Mateo, CA (US); Casey C. Lynch, San Francisco, CA (US); Alexander Strikovsky, Daly City, CA (US)

(73) Assignee: Aspira Biosystems, Inc., South San Francisco, CA (US)

(*) Notice: Subject to any disclaimer, the term of this patent is extended or adjusted under 35 U.S.C. 154(b) by 748 days.

(21) Appl. No.: 10/121,331

(22) Filed: Apr. 11, 2002

(65) Prior Publication Data

US 2003/0165882 A1 Sep. 4, 2003

Related U.S. Application Data

(60) Provisional application No. 60/283,257, filed on Apr. 11, 2001.

(51) Int. Cl.
*C12Q 1/00* (2006.01)

(52) U.S. Cl. .......................... 435/4; 427/2.13; 436/518; 436/531; 436/535

(58) Field of Classification Search ................ 436/518, 436/524, 531, 535; 435/4; 427/2.13
See application file for complete search history.

(56) References Cited

U.S. PATENT DOCUMENTS

| | | | |
|---|---|---|---|
| 4,962,154 A | 10/1990 | Pollock et al. | |
| 5,110,833 A | 5/1992 | Mosbach | |
| 5,310,648 A | 5/1994 | Arnold et al. | |
| 5,372,719 A | 12/1994 | Afeyan et al. | |
| 5,453,199 A | 9/1995 | Afeyan et al. | |
| 5,541,342 A | 7/1996 | Korhonen et al. | |
| 5,587,273 A | 12/1996 | Yan et al. | |
| 5,630,978 A | 5/1997 | Domb | |
| 5,641,539 A | 6/1997 | Afeyan et al. | |
| 5,728,296 A | 3/1998 | Hjerten et al. | |
| 5,756,717 A | 5/1998 | Paliwal et al. | |
| 5,786,428 A | 7/1998 | Arnold et al. | |
| 5,801,221 A | 9/1998 | Tanaka et al. | |
| 5,814,223 A | 9/1998 | Hjerten et al. | |
| 5,821,311 A | 10/1998 | Mosbach et al. | |
| 5,858,296 A | 1/1999 | Domb | |
| 5,872,198 A | 2/1999 | Mosbach et al. | |
| 5,916,445 A | 6/1999 | Hjerten et al. | |
| 5,959,050 A | 9/1999 | Mosbach et al. | |
| 5,994,110 A | 11/1999 | Mosbach et al. | |
| 6,051,372 A | 4/2000 | Bayerl et al. | |
| 6,057,377 A | 5/2000 | Sasaki et al. | |
| 6,217,901 B1 | 4/2001 | Perrott et al. | |

(Continued)

FOREIGN PATENT DOCUMENTS

WO   WO 95/21673   8/1995

(Continued)

OTHER PUBLICATIONS

Rachkov et al., entitled:"Recognition of Oxytocin and Ocytocin-related Peptides in Aqueous Media Using a Mlecularty Imprinted Polymer Synthesized by the Epitope Approach" Elsevier Science B.V., 2000, pp. 111-118.

(Continued)

*Primary Examiner*—Christopher L. Chin
(74) *Attorney, Agent, or Firm*—Patterson & Sheridan, LLP

(57) ABSTRACT

The present invention provides imprint bead compositions useful for capturing, isolating, detecting, analyzing and/or quantifying molecules in a sample. The imprint bead compositions comprise a matrix material having imprint cavities of a template molecule or molecules imprinted thereon wherein a substantial number of the imprint cavities are located at or near the surface of the matrix material.

24 Claims, 13 Drawing Sheets

U.S. PATENT DOCUMENTS 6,310,110 B1    10/2001    Markowitz
6,379,599 B1    4/2002    Viadya et al.
6,458,599 B1    10/2002    Huang

FOREIGN PATENT DOCUMENTS

WO    WO 01/09035 A1    2/2001
WO    WO 01/61354 A1    8/2001
WO    WO 01/61355 A1    8/2001

OTHER PUBLICATIONS

Rachkov et al., entitled:"Towards Molecularty Imprinted Polymer Selective to Peptides and Proteins. The Epitope Approach" Elsevier Science B.V., Biochemica et Biophysica Acta 1544, 2001, pp. 255-266.

Markowitz et al., entitled:"Catalytic Silica Particles via Template-Directed Molecular Imprinting" American Chemical Society, 2000, published on the web Dec. 1999, pp. 1759-1765.

Leonhardt et al., entitled:"Enzyme-Mimicking Polymers Exhibiting Specific Substrate Binding and Catalytic Functions" Elsevier Science B.V., 1987, pp. 285-290.

Lederer et al., entitled:"Molecular Imprinting of Amino Acid Derivatives in Macroporous Polymers" Elsevier Science B.V., 1985, pp. 1-10.

Glad et al., entitled:"Use of Silane Monomers for Molecular Imprinting and Enzyme Entrapment in Polysiloxane-Coated Porous Silica" Elsevier Science B.V., 1985, pp. 255-266.

Peppas et al., entitiled:"Poly(ethylene glycol)-Containing Hydrogels in Drug Delivery" Elsevier Science B.V., 1999, pp. 81-87.

Cormack and Mosbach, 1999 "Molecular Imprinting: Recent Developments And The Road Ahead." *Reactive and Functional Polymers 41*:115-124.

Dickey, 1949, "The Preparation Of Specific Adsorbents," *Proc. Natl. Acad. Sci. U.S.A.* 35(5):227-229.

Markowitz et al, 1999, "Catalytic Silica Particles via Template-Directed Molecular Imprinting" *Langmuir 2000*: 1759-1765.

Wulff, 1998, "Fitting Molecules Into Polymeric Receptors," *Chemtech* 28:19-26.

Nikolaos et al. Poly(ethylene glycol)-containing hydrogels in drug delivery. Journal of Controlled Release, Nov. 1999, vol. 62, pp. 81-87.

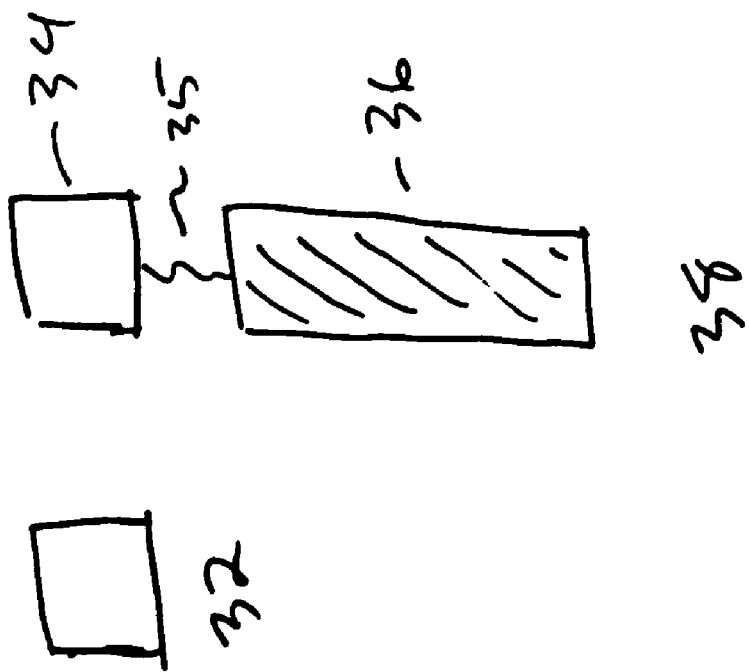

A

B

C

D

SEQUENCE LISTING

```
<160> NUMBER OF SEQ ID NOS: 5

<210> SEQ ID NO 1
<211> LENGTH: 7
<212> TYPE: PRT
<213> ORGANISM: equine

<400> SEQUENCE: 1

Leu Lys Lys Ala Thr Asn Glu
1               5

<210> SEQ ID NO 2
<211> LENGTH: 7
<212> TYPE: PRT
<213> ORGANISM: human

<400> SEQUENCE: 2

Tyr Val Val Asp Thr Ser Lys
1               5
```

-continued

```
<210> SEQ ID NO 3
<211> LENGTH: 7
<212> TYPE: PRT
<213> ORGANISM: bovine

<400> SEQUENCE: 3

Ser Thr Gln Thr Ala Leu Ala
1               5

<210> SEQ ID NO 4
<211> LENGTH: 7
<212> TYPE: PRT
<213> ORGANISM: human

<400> SEQUENCE: 4

Asp Met Ile Pro Ala Gln Lys
1               5

<210> SEQ ID NO 5
<211> LENGTH: 7
<212> TYPE: PRT
<213> ORGANISM: human

<400> SEQUENCE: 5

Ser Gln Asn Pro Gln Ser Gln
1               5
```

INVERSE EMULSION METHODS OF MAKING POLYMERIC IMPRINT BEADS

CROSS-REFERENCE TO RELATED APPLICATIONS

This application claims priority under 35 U.S.C. §119(e) to U.S. Patent Application No. 60/283,257, filed Apr. 11, 2001, which is hereby incorporated herein by reference.

1. FIELD OF THE INVENTION

The present invention is directed to methods of making novel molecular imprint beads in inverse emulsions and the imprint beads made by such methods. Imprint beads comprise cavities that have shapes that complements the shape of a template molecule used to make the beads. Imprint beads made by this method can be used to selectively bind or capture the template molecule, or other molecules having a portion or moiety that corresponds in shape to the template molecule.

2. BACKGROUND OF THE INVENTION

Conventional techniques of molecular imprinting have provided useful methods for the preparation of matrices that are capable of selectively capturing a target molecule. To prepare a molecular imprint, a matrix is formed around a template molecule. After the matrix has formed and the template molecule has been removed, the resulting molecular imprint can then be used to selectively capture the template molecule. As early as 1949, a silica gel was created that selectively bound a dye (Dickey, 1949, Proc. Natl. Acad. Sci. USA 35:227–229). Recently, an imprint prepared with phenyl-α-D-mannopyranoside was sufficiently selective to resolve a racemic mixture of the saccharide (Wulff, 1998, Chemtech 28:19–26).

Current methods form imprints of template molecules in organic polymers (Wulff, 1998, supra). To create cavities of defined shape, polymerizable molecules are bound, covalently or noncovalently, to a template molecule (Wulff, 1998, supra). The resulting complex is then copolymerized in the presence of a large amount of a cross-linking reagent (Wulff, 1998, supra). The templates are then removed, leaving cavities having defined shapes (Wulff, 1998, supra). Molecular imprints made by such a technique display selective binding for the template molecule. Molecular imprints have been used for chromatographic separation, immunoassays, chemosensors, and even catalysis (Wulff, 1998, supra).

However, failings of conventional techniques limit the broad application of molecular imprints. According to a recent review, two issues "of great importance" that limit the application of conventional molecular imprints are their limited capacity and the heterogeneity of imprint cavities (Cormack and Mosbach, 1999, Reactive and Functional Polymers 41:115–124). When conventional imprints are used to capture the template molecule, it is believed that their random distribution of imprint cavities limits their accessibility to the template molecules. Typically, the majority of cavities are localized in the interior of the molecular imprint. These interior cavities are less accessible to the template molecule than cavities localized at the surface of the imprint. This effect not only reduces the number of cavities available for binding, but also limits the types of molecules that can be bound or captured. In particular, large molecules that cannot penetrate the matrix material of a molecular imprint can bind only at surface cavities. Thus, conventional molecular imprints are not advantageous for specifically capturing large molecules such as proteins, nucleic acids and other macromolecules.

The binding capacity of conventional imprints is also reduced by the random orientations of their cavities. In forming a molecular imprint by conventional techniques, the template molecules are randomly oriented within the matrix. Thus, the corresponding molecular imprint cavities are also randomly oriented. If a particular orientation of an imprint cavity binds a target molecule more efficiently than other orientations, then only the fraction of cavities that are properly oriented will display efficient binding. The random orientation of the cavities, combined with their random distribution throughout the imprint, exacerbates the poor binding capacity of conventional molecular imprints.

Finally, conventional techniques suffer from leakage of the template molecule (Wulff, 1999, supra). When the imprint is formed, many template molecules are trapped deep within the imprint matrix. Trapped template molecules that are not removed may leak during the use of the molecular imprint. Leakage of the template molecule contaminates the sample and hinders application of conventional molecular imprints, particularly applications that involve binding or capturing minute amounts of the template molecule. For instance, this shortcoming of conventional molecular imprints has particularly limited their application in the pharmaceutical industry (Wulff, 1999, supra).

What is needed are novel molecular imprints that overcome the shortcomings of conventional molecular imprints. Novel methods of making molecular imprints with oriented and accessible binding cavities, and less leakage of the template molecule, will have improved capacity, specificity, and application, particularly for large molecules such as proteins, nucleic acids and polysaccharides.

3. SUMMARY OF THE INVENTION

In one aspect, the present invention provides methods of making "oriented" or "surface" imprint bead compositions. An imprint bead is prepared using an inverse emulsion system in which the template molecules are localized at the interface of the water particles (non-continuous phase) of the emulsion. In the method, an imprint is prepared with an amphipathic conjugate molecule comprising a template moiety attached to a tail moiety, optionally by way of a spacer or linker. The template moiety constitutes the template around which the imprint cavities are created. The template moiety of the conjugate molecule should be soluble in the non-continuous phase of the inverse emulsion, and the tail moiety should be soluble in the continuous phase of the inverse emulsion such that the conjugate molecule is capable of partitioning to an interface of the inverse emulsion.

To make an imprint bead, the conjugate molecule and the matrix material (in its fluid state) are mixed with a solvent system that is capable of forming an inverse emulsion. The solvent system typically comprises a polar solvent, such as water, a solvent immiscible with the polar solvent and optionally a suitable surfactant or dispersant. The surfactant or dispersant and the relative volumes of the phases are selected so that the solvent system is capable of forming an inverse emulsion under the appropriate conditions.

When mixed or dissolved in the solvent system, the conjugate molecule partitions at an interface of the solvent system, with the template moiety of the conjugate residing or partitioning in the polar solvent and the tail moiety of the conjugate residing or partitioning in the non-polar solvent. The matrix material is chosen so that it partitions into or comprises the polar solvent phase of the solvent system. The conjugate molecule, the matrix material and the solvent system are then mixed under conditions in which the mixture forms an inverse emulsion, e.g., by stirring, by shearing, by sonication or by other means of agitation. Once the emulsion has formed, conditions under which the matrix material changes from a fluid state to a semisolid or solid state are applied or effected. Changing the physical state of the matrix material in the presence of the template moiety results in the formation of a solid or semisolid matrix having the template moieties entrapped at the surface of the matrix. Moreover, owing to the partitioning of the conjugate molecule across the two phases of the inverse emulsion, the template moieties are oriented with respect to the polar/non-polar solvent interface. The tail moiety remains partitioned in the non-polar solvent phase of the two-phase system and does not become entrapped by the solid or semisolid matrix material. The conjugate molecules are then removed, yielding a solid or semisolid matrix bead comprising cavities located at or near its surface of the matrix bead that complement the shape of the template moieties. This resultant product is a "surface" or "oriented" imprint bead.

The surface or oriented imprint beads are useful for capturing, isolating, detecting, analyzing and quantifying potentially any target molecule. Structurally, the template moiety of the conjugate molecule can be identical to or similar to the target molecule. Alternatively, the template moiety can correspond to a portion of a larger target molecule. A surface or oriented imprint bead of a template moiety that corresponds to a portion of a larger target molecule is particularly useful for capturing, isolating, detecting, analyzing and quantifying macromolecular target molecules such as proteins, nucleic acids, carbohydrates and other macromolecules. Methods for constructing template moieties useful for making molecular imprints capable of capturing, isolating, detecting, analyzing and quantifying larger target macromolecules are described in detail in copending application Ser. No. 09/507,300, filed Feb. 18, 2000, and corresponding PCT publication WO 01/61355, published 23 Aug. 2001, which are hereby incorporated by reference in their entirety.

Matrix materials that can comprise the imprint compositions of the invention include substances that are capable of undergoing a physical change from a fluid state to a semisolid or solid state. In the fluid state, matrix material molecules move easily amongst themselves, and the material retains little or no definite form. A matrix material in the fluid state can be mixed with other compounds including template moieties or conjugate molecules. In the semi-solid or solid state, the matrix material is capable of defining and retaining cavities that complement the shape of template moieties dispersed or dissolved thereon. Non-limiting examples of such matrix materials include monomers that are polymerizable in aqueous or polar solution such as acrylamide, and mixtures of such monomers and cross-linking reagents.

The imprint beads of the invention may take a variety of different shapes and sizes which can be varied by varying the imprint conditions. In particular, the size (average diameters) of the imprint beads is controlled largely by the size (average diameters) of the droplets in the continuous (oil) phase of the inverse emulsion and may vary over quite a wide range. For example, the imprint beads may have average (sizes) diameters that range from nanometers to micrometers, or even larger. The average (sizes) diameters of the droplets in the continuous phase are in turn dependent upon, among other factors, the compositions of the two phases, the dispersant or surfactant selected, the amount of surfactant or dispersant, the agitation used to create the emulsion, the temperature and other factors known to those of skill in the art. The surface area of the beads in the inverse emulsion system is an important factor affecting imprint capacity and performance, and surface area is inversely proportional to bead size.

Thus, a significant advantage of the methods of the invention is the ability to select combination of these variable to yield imprint beads having specified average (sizes) diameters.

In addition, parameters for creating emulsions in which the distribution of the average diameters of the droplets is narrow or uniform are well-known. Thus, an additional advantage of the methods of the invention is the ability to produce imprint beads of a specified average diameter that have narrow diameter distributions without having to sieve the beads. Of course, sieving may also be used to achieve collections of imprint beads that are nearly homogenous in average diameter, and/or specified surface area.

The methods and compositions of the invention provide significant advantages over currently available molecular imprinting technologies. Unlike known imprinting techniques, the imprint cavities of the imprint beads of the present invention are oriented and localized at the surface of the matrix material. Imprint beads according to the invention are more sensitive than conventional imprints, in part because the imprint beads have a higher number of imprint cavities accessible at or near their surface for binding a target molecule. The greater density of accessible imprint cavities also reduces the amount of nonspecific binding of the imprint beads, further increasing the sensitivity of the imprint beads of the present invention. In particular, the imprint beads of the invention have a significantly improved capacity for binding large molecules that cannot penetrate into the matrix material.

In addition, because the template moieties are oriented during the formation of the imprint beads, the imprint beads of the present invention have cavities that are oriented with respect to the surface of the imprint beads, as compared with the randomly oriented cavities obtained using conventional techniques. Proper orientation of imprint cavities can improve the binding properties of a molecular imprint. In particular, when an imprint cavity is complementary to a portion of the molecule to be captured by the imprint, then the orientation of the cavity has a significant effect on its binding efficiency. For instance, referring to FIG. 1, if imprint cavities are complementary to the carboxy-terminal portion of polypeptide 2, then imprint cavity 4, which is accessible at its amino terminal end, will bind polypeptide 2 more effectively than imprint cavity 6, which is not accessible at its amino terminal end. Imprint cavity 6 might not bind macromolecule 2 at all. Imprint beads can be prepared according to the present invention so that almost every cavity is uniformly oriented to bind the target molecule.

Finally, the methods and compositions of the present invention are also useful for applications that are sensitive to template leakage, such as dilute mixtures of molecules where template leakage is a problem for conventional imprints. Compared to conventional molecular imprints that can entrap template moieties in internal cavities deep within their matrices, imprint beads retain far fewer template moieties within their solvent-accessible cavities.

The methods and imprint beads of the invention have widespread applicability, ranging from the detection and/or isolation of specific molecules of interest from samples, to the capture, isolation, analysis and/or quantification of pluralities of molecules from complex mixtures for applications such as, for example, expression profiling, to the discovery of novel members of known classes of molecules and/or completely new types of molecules altogether.

4. BRIEF DESCRIPTION OF THE FIGURES

FIG. 1 provides an illustration comparing a properly oriented imprint cavity with an improperly oriented imprint cavity of the same template moiety;

FIG. 2 provides an illustration comparing conventional molecular imprints with an imprint bead of the invention;

FIG. 3A illustrates a conjugate molecule useful for preparing an imprint bead that can capture a target molecule;

Figure 6:

FIG. 6 shows a silver stained gel of protein eluted from ADH imprinted beads after the beads were exposed to a cell lysate spiked with alcohol dehydrogenase (1% of total protein). Lane 1 is the protein mixture presented to the beads. Lane 2 is the protein eluted from the ADH imprinted beads.

Figure 7:
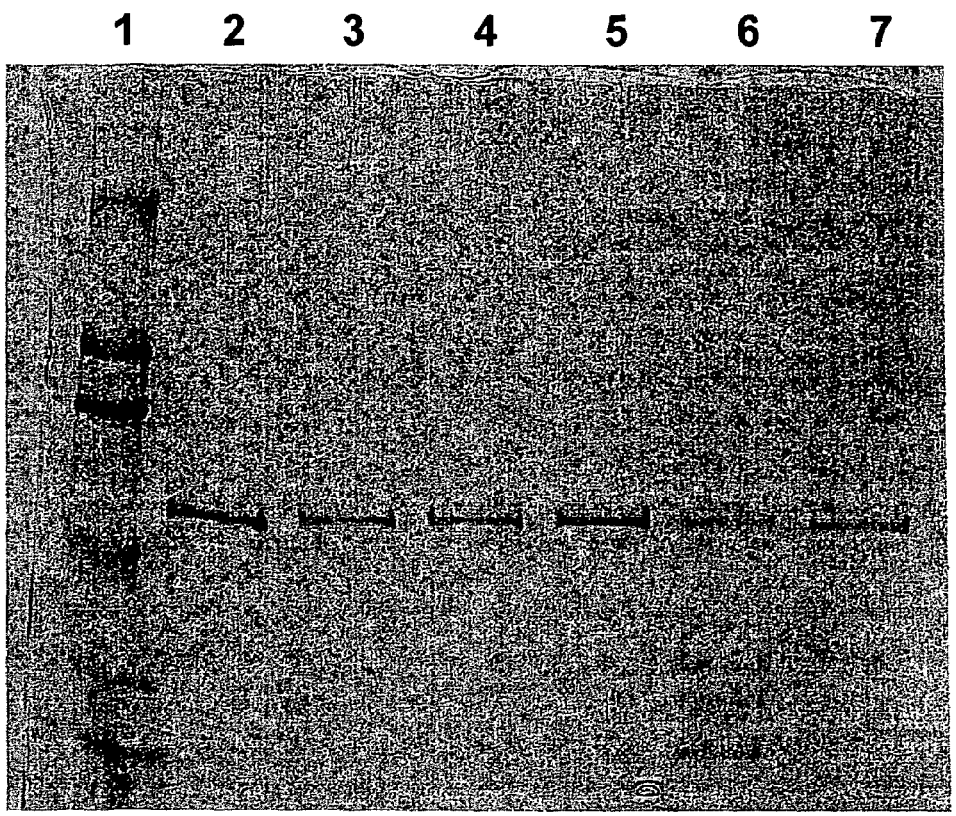

FIG. 7 shows a silver stained gel providing the results of a peptide competition experiment. Lane 1 provides molecular weight markers. Lane 2 shows that non-imprinted control beads capture no estrogen receptor (ER) protein from solution. Lane 3 shows that beads imprinted beads with a seven amino acid peptide, SQNPQSQ, corresponding to the C-terminus of estrogen receptor (ER imprinted beads) capture and thus sequester estrogen receptor from solution. Lanes 4 and 5 demonstrate that excess ER peptide, SQNPQSQ, compete with full length estrogen receptor for binding with the ER imprinted beads, thus decreasing the amount estrogen receptor sequestered from solution. Lane 4 has a 100-fold molar excess of the ER peptide relative to estrogen receptor. Lane 5 has a 500-fold molar excess of ER peptide. Lanes 6 and 7 demonstrate that a seven amino acid peptide, STQTALA, that is unrelated to estrogen receptor fails to compete with estrogen receptor for binding sites on the ER imprinted beads. Thus the ER imprinted beads selectively capture estrogen receptor. Lane 6 has a 100-fold molar excess of peptide STQTALA. Lane 7 has a 500-fold molar excess of peptide STQTALA. Only the related peptide interferes with capture of estrogen receptor by ER imprinted beads.

Figure 8:
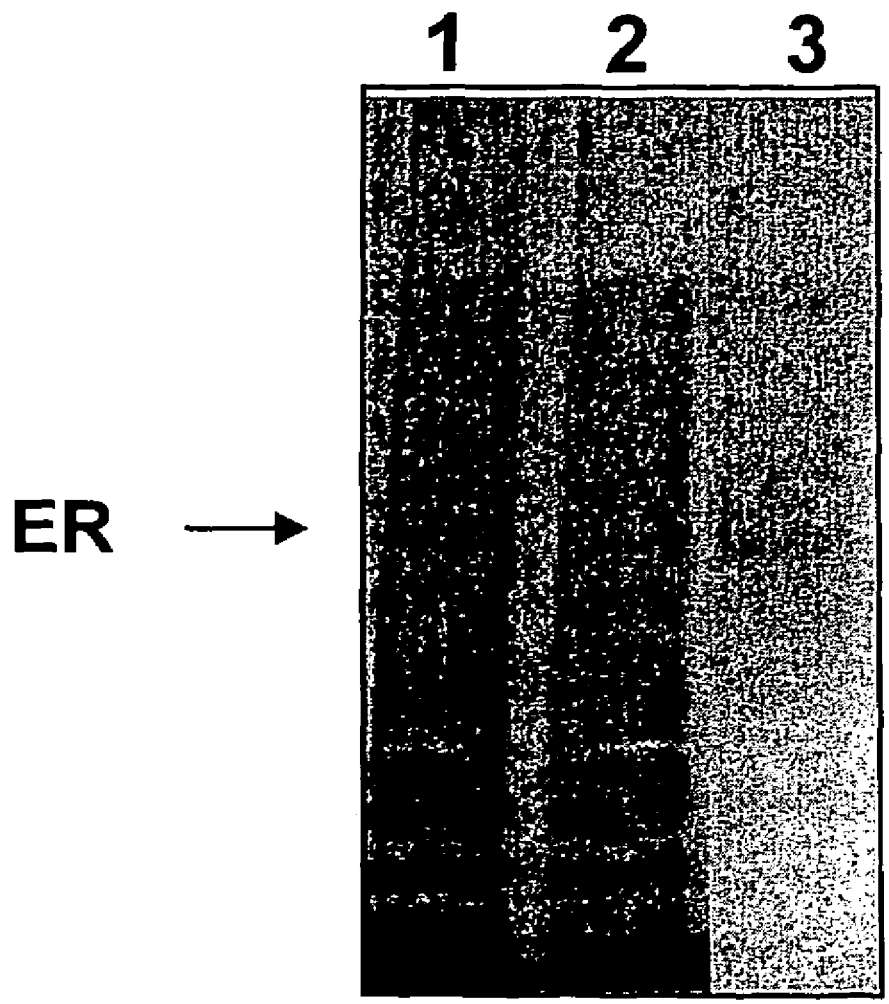

FIG. 8 shows a silver stained gel of protein eluted from ER imprinted beads after the beads were exposed to a cell lysate spiked with estrogen receptor. Lane 1 is the protein mixture presented to the beads. Lane 2 is the supernatant containing protein not bound by the beads. Lane 3 is the protein eluted from the ER imprinted beads.

Figure 9:
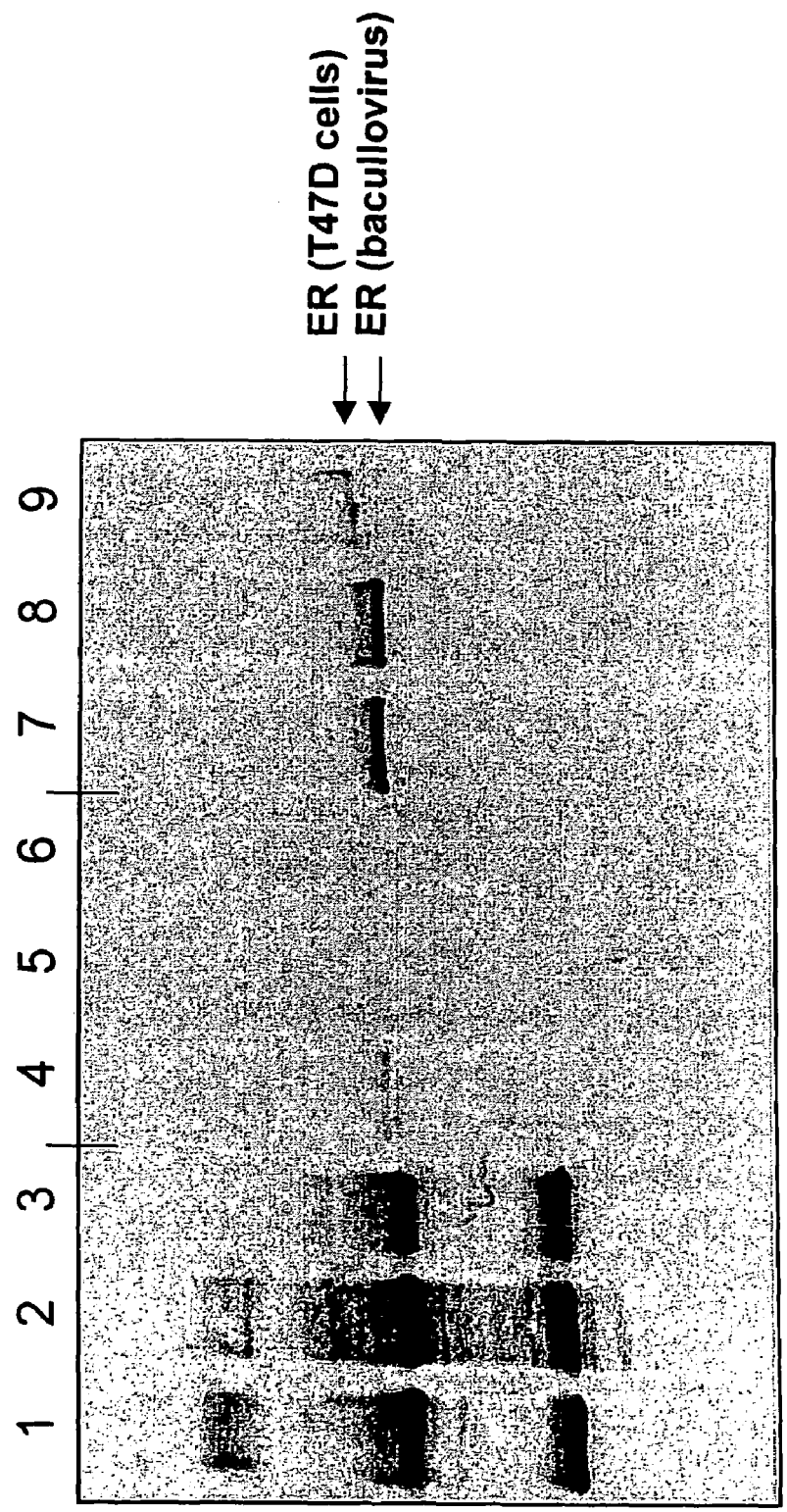

FIG. 9 shows a western blot of protein eluted from beads exposed to a cell lysate spiked with estrogen receptor. Lane 1 is recombinant estrogen receptor. Lane 2 is the cell lysate spiked with estrogen receptor. Lane 3 is the cell lysate alone. Lane 4 is the protein eluted from non-imprinted control beads after being exposed to recombinant estrogen receptor alone. Lane 5 is the protein eluted from non-imprinted control beads exposed to cell lysate spiked with estrogen receptor. Lane 6 is the protein eluted from non-imprinted control beads exposed to cell lysate alone. Lane 7 is the protein eluted from ER imprinted beads exposed to recombinant estrogen receptor alone. Lane 8 is the protein eluted from ER imprinted beads exposed to cell lysate spiked with estrogen receptor. Lane 9 is the protein eluted from ER imprinted beads exposed to cell lysate alone.

Figure 10:
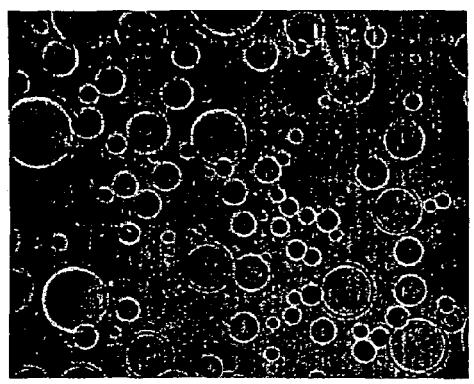
Figure 10:
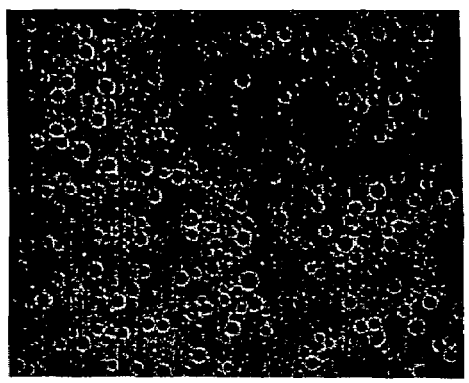
Figure 10:
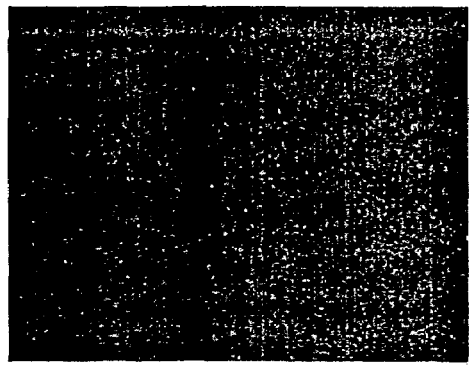
Figure 10:
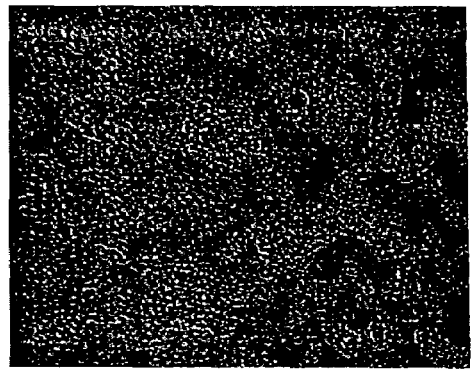

FIG. 10A shows acrylamide beads formed by stirring together aqueous and organic phases prior to polymerization.

FIG. 10B shows acrylamide beads formed by vortexing the aqueous and organic phases prior to polymerization.

FIG. 10C shows acrylamide beads formed by syringe homogenizing the organic and aqueous phases prior to polymerization.

FIG. 10D shows acrylamide beads formed by sonicating the aqueous and organic phases prior to polymerization.

Figure 11A:
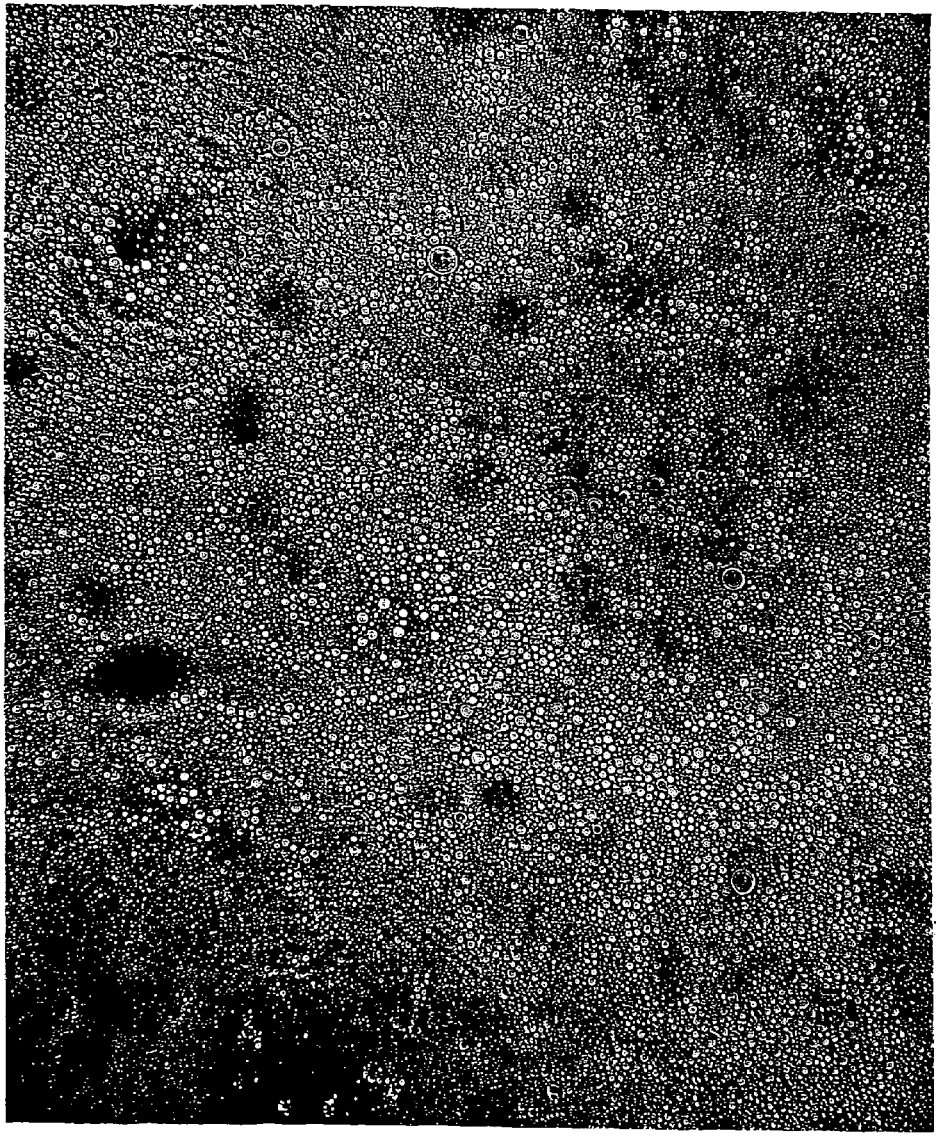

FIG. 11A shows an inverse emulsion of the present invention prior to polymerization.

Figure 11B:
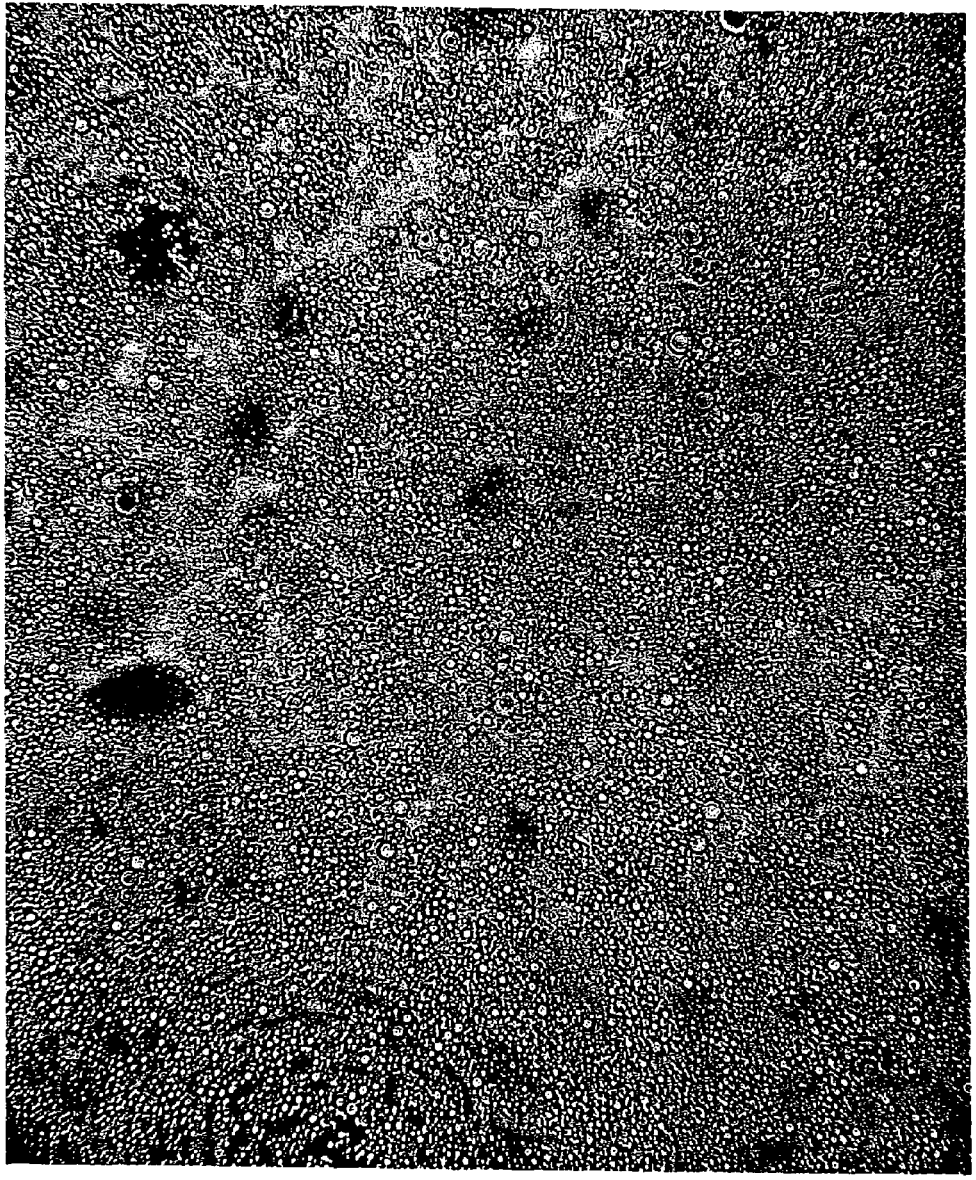

FIG. 11B shows the same inverse emulsion of FIG. 11A, after polymerization.

5. DETAILED DESCRIPTION OF THE INVENTION

Current molecular imprints lack ideal binding specificity and capacity. The specificity and capacity of current molecular imprints are impaired by the poor accessibility of many of their cavities and by the heterogeneity of those cavities. In addition, current molecular imprints suffer from chronic leakage of template molecules.

The present invention provides methods and compositions that overcome these and other limitations of molecular imprinting. The invention is based, in part, on the finding that imprinting in inverse emulsions with amphiphilic conjugate molecules yields imprint beads in which a substantial number or fraction of the resultant imprint cavities are oriented and localized at or near the surface of the imprint beads. The imprint beads of the present invention thus have cavities that are more accessible than those of prior imprints and that are properly oriented for binding a target molecule. Because the imprint beads trap fewer template molecules internally, the imprint beads compositions of the invention also exhibit less template leakage during use than conventional molecular imprints. Overall, the imprint beads of the present invention display greater capacity and more reproducible binding when compared to conventional molecular imprints.

5.1 Abbreviations

As used herein, the abbreviations for the genetically encoded L-enantiomeric amino acids are conventional and are as follows:

| Amino Acid | One-Letter Symbol | Common Abbreviation |
|---|---|---|
| Alanine | A | Ala |
| Arginine | R | Arg |
| Asparagine | N | Asn |
| Aspartic acid | D | Asp |
| Cysteine | C | Cys |

-continued

| Amino Acid | One-Letter Symbol | Common Abbreviation |
| --- | --- | --- |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The abbreviations used for the D-enantiomers of the genetically encoded amino acids are lower-case equivalents of the one-letter symbols. For example, "R" designates L-arginine and "r" designates D-arginine. The abbreviations used for D-enantiomeric amino acids may also be indicated by the three-letter abbreviation preceded by a "D-". For examples, "Ala" designates L-alanine, whereas "D-Ala" designates D-alanine. When a polypeptide sequence is represented as a series of three-letter or one-letter amino acid abbreviations, it will be understood that the left-hand direction is the amino terminal direction and the right-hand direction is the carboxy terminal direction, in accordance with standard usage and convention.

5.2 Methods of Making Imprint Beads

In one aspect, the present invention provides methods of making imprint beads. In general, a solvent system capable of forming an inverse emulsion with a conjugate molecule partitioned at its interface is used to generate an imprint bead.

5.2.1 Solvent Systems

The methods of forming an imprint bead composition use an amphipathic conjugate molecule in an inverse emulsion. An "inverse emulsion" refers to an emulsion in which the polar, typically aqueous, phase is the discontinuous phase, and the non-polar, typically oil, phase is the continuous phase.

The sizes (diameters) of the aqueous droplets within an inverse emulsion of the invention will typically be greater than 1 µm. The inverse emulsion before polymerization is a thermodynamically unstable condition that must be formed and maintained by shearing and/or surfactant stabilization. This is in contrast to microemulsions, which have droplets smaller than 0.1 µm in diameter (typically in the range of 10–20 nm) that are formed in a thermodynamically stable state before polymerization using high levels of micelle-forming surfactant(s). A microemulsion comprising polymerizable monomers forms spontaneously and will remain in the emulsion state indefinitely. Before and during polymerization, the droplets of a microemulsion dynamically exchange monomers and other chemical components with one another.

In stark contrast, the droplets of an inverse emulsion do not exchange monomers with one another, and as such are a chemically static system, where the particles that are formed during emulsification polymerize as distinct and independent particles. Inverse emulsions are ideally suited to formation of useful imprints of the invention, because the chemically static nature of the particle surface before polymerization allows for optimal interaction of the amphiphilic template molecules with the polymerizing matrix. Furthermore, beads larger than 1 µm are very useful for biological separations and analyses because they can be isolated, purified, and manipulated by filtration and centrifugation. Also, the larger beads formed by inverse emulsion polymerization can be packed into columns for chromatography and purification. Such techniques are not compatible with microemulsion particles of less than 0.1 µm diameter, which are colloidal systems where the particles remain suspended indefinitely by Brownian motion.

The conjugate molecule, having a template moiety and a tail moiety, partitions to an interface of the inverse emulsion, and a solid or semi-solid matrix is formed in a water phase of the inverse emulsion. The resulting matrix comprises an imprint bead of the portion of conjugate molecule at the surface of the matrix defined by the interface.

Figure 3B:
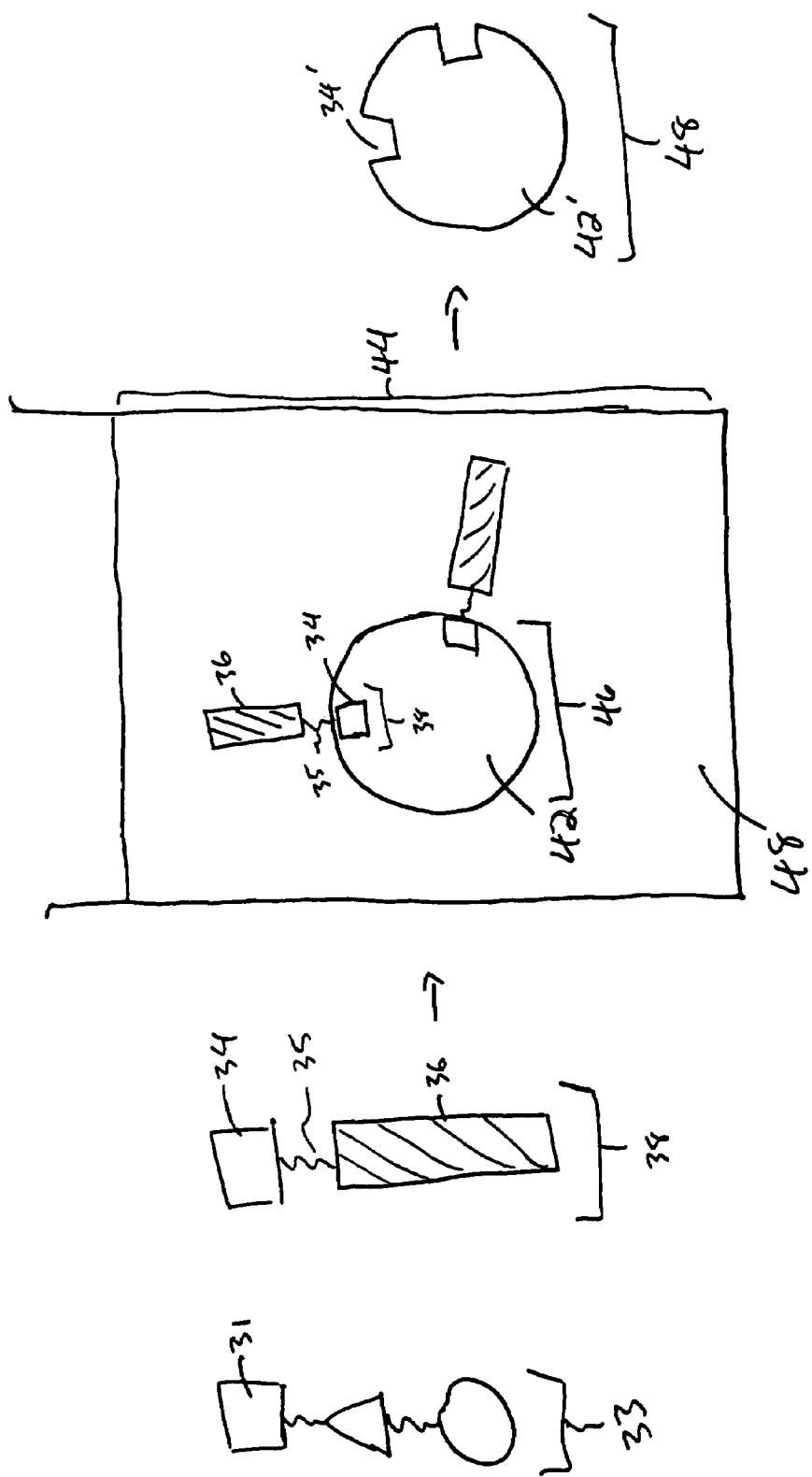
FIG. 3B illustrates a method of preparing an imprint bead of the invention utilizing a solvent system capable of forming an inverse emulsion.

General inverse emulsion methods for preparing an imprint bead of the present invention are illustrated in FIG. 3A and FIG. 3B. Referring to FIG. 3B, to prepare an imprint bead that is useful for capturing target molecule 32, conjugate molecule 38 is first prepared and used to form the imprint. Conjugate molecule 38 comprises a template moiety 34 and a tail moiety 36. The template moiety 34 and tail moiety 36 are linked together, optionally by way of a linker 35. As illustrated in FIG. 3A, template moiety 34 may be the target molecule to be captured (32). Alternatively, as illustrated in FIG. 3B, template moiety 34 may correspond to a portion (31) of a larger target molecule 33. Template moieties that correspond to portions of larger target molecules, as well as methods describing how they are designed and obtained, are described in more detail, infra.

Regardless of the identity or source of template moiety 34, tail moiety 36 has a hydrophobicity that complements, or is the opposite of, the hydrophobicity of template moiety 34. Template moiety 34 is typically hydrophilic, and tail moiety 36 is typically hydrophobic. When dissolved in a solvent system that is capable of forming an inverse emulsion, conjugate molecule 38 can partition at an interface of the inverse emulsion. The degree of hydrophobicity of tail moiety 36 will depend on a variety of factors, including among others, the choice of solvents and the degree of or hydrophilicity of template moiety 34. Methods for determining the hydrophobicities or hydrophilicities of template moiety 34 and tail moiety 36 are described in more detail, infra. Tail moieties 36, and optional linker moieties 35 (discussed below) that yield conjugates 38 capable of partitioning at the interface of the two-phase system for particular solvents and template moieties are within the capabilities of those of skill in the art.

The solvent system comprises a polar solvent, a non-polar solvent and an optional surfactant or dispersant. The choice of solvents and surfactants or dispersants used to create the solvent system is not critical. Virtually any combination of solvents and surfactants or dispersants that are capable of forming an inverse emulsion, that are compatible with the conjugate molecule, and that permit the conjugate molecule to partition at the interface, preferably with the template moiety residing in one phase and the tail moiety in the other, can be used.

Non-limiting examples of suitable polar (hydrophilic) solvents include water (optionally including chaotropes, buffering agents, salts, etc.), lower alkyl alcohols (e.g., methanol, ethanol, propanol, isopropanol, etc.), acetonitrile, dimethylsulfoxide (DMSO), dimethylformamide, glycerol, ethylene glycol, etc., as well as mixtures of any of these solvents. Water is a preferred polar solvent.

Non-limiting examples of suitable non-polar (hydrophobic) solvents include acetone, ether, benzene, hydrocarbons such as hexane, cyclohexane, heptane, etc., methylene chloride, carbon tetrachloride, chloroform, petroleum ether, mineral oil, light mineral oil, silicone oil, paraffins, phenol, benzene, toluene, etc., as well as combinations of any of the above. Preferred non-polar solvents include light mineral oil, benzene, toluene, hexane, cyclohexane and inert oils and paraffins such as those sold under the tradename ISOPAR M (Exxon). A particularly suitable non-polar solvent is ISO-PAR M.

The optional surfactant or dispersant should render the solvent system capable of forming an inverse emulsion. For example, in a solvent system comprising the preferred solvents water and ISOPAR M, suitable surfactants or dispersants include those with a hydrophilic/lipophilic balance ("HLB") between about 4 to about 6. Suitable surfactants and dispersants are discussed in Kiatkamjornwong and Phunchareon, 1999, J. Applied Polymer Sci. 72: 1349–1366, and in Alexandridis, 1996, Curr. Opin. Colloid Interface Sci. 1:190–501, the contents of which are hereby incorporated by reference in their entireties. Preferred surfactants or dispersants have an HLB between about 3 and about 6. For a description of HLB values and methods for measuring HLB values, see Evans et al., 1994, The *Colloidal Domain*, VCH Publishers, New York, N.Y., pp.492. Non-limiting examples of suitable surfactants or dispersants include sorbitan oleates, block copolymers and glycerol esters, including by way of example and not limitation, Arlacel 83 (Uniqema), KLE 3736 (Goldschmidt AG), Span 80 (Sigma), Hypermer B239 (Uniqema) and Hypermer B246SF (Uniqema).

In certain embodiments of the invention, the conjugate molecule can serve as the optional surfactant or dispersant. Since conjugate molecules have a hydrophilic template moiety and a hydrophobic tail moiety, conjugate molecules have surfactant or dispersant properties. In particular, conjugate molecules that have HLB values in the range of about 4 to about 6 are effective surfactants or dispersants in the methods of the invention.

The solvents and surfactants or dispersants may be used in a variety of different combinations to create inverse emulsions. The actual choice of solvents and surfactants or dispersants will depend upon, among other things, the properties of the conjugate molecule and the desired properties of the imprint beads. Suitable solvent systems will be apparent to those of skill in the art. Preferably, the solvents selected are non-toxic and non-teratogenic. A preferred solvent system for most applications comprises water (or aqueous buffer), the inert oil ISOPAR M and a surfactant selected from the group consisting of Arlacel 83 and KLE 3736.

The solvent system also comprises a matrix material that is soluble in the water phase of the solvent system. Matrix material 42 is a compound or mixture of compounds that is capable of undergoing a change of physical state from a fluid state to a solid or semisolid state. In the fluid state, the molecules of matrix material 42 move easily among themselves, and the material retains, little or no definite form. A matrix material in the fluid state can be mixed with other compounds, including template moieties or conjugate molecules. Matrix material 42 may comprise virtually any compound or mixture of compounds that is compatible with template molecule 34 and conjugate molecule 38 and that is capable of undergoing a change of physical state to form a solid or semisolid such that the changed form is capable of retaining shaped cavities. The physical state change can be induced by virtually any means, including thermal, chemical and/or electromagnetic processes. Preferred matrix materials include matrix materials that are polymerizable in aqueous solvents. Particularly preferred matrix materials include acrylamide and a combination of acrylamide and a suitable cross linking molecule such as N-N'-ethylene bisacrylamide, N-N'-methylene bisacrylamide and polyethylene bisacrylamide.

During the embedding process, matrix material 42 changes physical state, or "hardens," from a fluid state to a solid or a semisolid state ("hardened") 42' in the presence of template moiety 34. Solid or semisolid matrix 42' is sufficiently shape-retaining to retain imprint cavities that complement the shape of template moiety 34. Removal of template moiety 34 from complex 46 yields imprint bead 48. In imprint bead composition 48, solid or semisolid matrix 42' defines cavities 34' that complement the topography of template moiety 34.

To prepare the imprint bead, as illustrated in FIG. 3B, conjugate molecule 38 is dispersed within composition 44. Composition 44 comprises matrix material 42, the two solvents, one hydrophobic (non-polar) and one hydrophilic (polar), and a surfactant or dispersant. As discussed above, the solvent system is capable of forming an inverse emulsion under the appropriate conditions, illustrated with water phase 46 and hydrophobic phase 48. Preferably, template moiety 34 is soluble in water phase 46 and tail moiety 36 is soluble in hydrophobic phase 48. Matrix material 42 is soluble in the same solution or phase in which the template moiety 36 is soluble.

Matrix material 42 is then induced to undergo a change of physical state, to form semisolid or solid matrix 42'. For example, if matrix material 42 is capable of polymerization, the change of physical state of matrix material 42 by initiating polymerization with an appropriate initiator. Since matrix material 42 is disposed throughout only one of the two phases—the phase comprising template moiety 34—as the matrix material hardens it entraps template moiety 34. Since the conjugate molecule 38 is localized/partitioned at the interface of the inverse emulsion, and the template moiety 34 is oriented in the water phase 46, removing template moiety 34 from the "hardened" matrix material 42' yields imprint cavities 34' that are oriented and localized at or near the surface of hardened matrix material 42'.

During the preparation process, composition 44 is typically agitated to form an emulsion of small droplets of water phase 42 in hydrophobic phase 48. Agitation thus yields an increased surface area of matrix material 42' and a greater number of surface imprint cavities 34' per volume of matrix material 42'. Suitable agitation and/or sonication conditions will be apparent to one of skill in the art. For instance, imprint beads can be prepared by stirring a solvent system comprising water, an inert oil and a surfactant under nitrogen for 12 hr. at 15° C. Mixing is also possible using vortex mixers, rotor-stator mixers, blenders, jet or orifice mixers or other mixers known in the art.

Although not illustrated, composition 44 can include a plurality of different conjugate molecules, each like conjugate molecule 38. Each conjugate molecule can comprise a template moiety that corresponds to a different molecule, or a portion thereof, yielding a variation of matrix 42' that can capture a plurality of different molecules. Alternatively, each conjugate molecule can comprise a template moiety that corresponds to a different portion of the same molecule, yielding a variation of matrix 42' that can bind or capture the molecule at a plurality of positions.

In one embodiment, matrix material 42 is a compound or mixture of compounds that undergoes a chemical or light induced liquid-to-solid state change, such as one or more polymerizable compounds. Examples of suitable polymerizable compounds include, but are not limited to, styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethylene)bis-acrylamide and trimethylolpropanetrimethacrylate, vinyl cyclodextrin, and polymerizable cyclodextrin. Further examples of polymerizable compounds that are useful for the preparation of imprint beads can be found in U.S. Pat. No. 5,858,296, which is hereby incorporated by reference in its entirety. Methods for inducing polymerization of these compounds are well-known. Preferred polymerizable compounds are those that are polymerizable in aqueous solution. A particularly preferred polymerizable compound is acrylamide.

The use of such polymerizable compounds is illustrated in FIG. 3B, where matrix material 42 is referred to in this paragraph as polymerizable compound 42. Referring to FIG. 3B, conjugate molecule 38 and a polymerizable compound 42 are mixed in a solvent that is suitable for polymerization of polymerizable compound 42. If necessary, an initiator for the polymerization of the polymerizable compound is included. Optionally, the conjugate molecule 38 can be covalently bound to the polymerizable compound 42, or the two can be allowed to form non-covalent complexes. Polymerization can by started by adding an appropriate catalyst such as ultraviolet radiation. After polymerization is complete, the conjugate molecule 38 is removed by diffusion, incubation in a chaotropic reagent such as urea or guanidine, or by other techniques known to those of skill in the art.

Cross-linking reagents can be optionally used with a polymerizable compound 42 to confer rigidity to the resultant imprint bead. The present invention contemplates any ratio of polymerizable compound to cross-linking reagent that yields an imprint bead of sufficient integrity to form a cavity whose shape corresponds to the shape of the template molecule. Cross-linking reagents are known to those of skill in the art. Examples of such cross-linking reagents can be found in U.S. Pat. No. 5,858,296. Preferred imprint beads are prepared with acrylamide and the cross-linking reagent N-N'-ethylene bisacrylamide.

In general, matrix material 42 and conjugate molecule 38 can be contacted under any conditions which permit matrix material 42 to change its physical state to a solid or semi-solid matrix 42'. For instance, matrix material 42 and conjugate molecule 38 can be contacted under native conditions or under denaturing conditions. As used herein, "native conditions" refers to those conditions under which the target molecule maintains its normal tertiary and quaternary structure. "Denaturing conditions" refer to those conditions that disrupt the tertiary and/or quaternary structure of the target molecule. Preferably, the conditions under which matrix material 42 embeds template moiety 34 are similar or identical to the conditions under which molecule 32 or 33 will be captured.

The concentration of matrix material 42, conjugate molecule 38, and an optional cross-linking reagent can be determined according to principles known to those of skill in the art of molecular imprinting. In particular, the number of cavities 34' in matrix 42' can be adjusted by varying the concentration of conjugate molecule 38. The concentration of conjugate molecule 38 can vary widely without deleteriously affecting the methods or resultant imprint bead compositions, typically from as low as 0.01 mM and as high as 1 M.

Once the matrix material 42' is in a solid or semi-solid state, hydrophobic phase 48 is removed from matrix material 42'. Conjugate molecule 38 is removed by diffusion or by other techniques known to those of skill in the art. If conjugate molecule 38 comprises a cleavable linker 35, then cleavable linker 35 can be cleaved to remove tail moiety 36. Template moiety 34 can then be removed via diffusion or other techniques as previously described. Methods for removing conjugate 38 via washing are described in the Examples.

The imprint beads can take on a variety of forms. Typically, the imprint beads take on the forms of the microparticles of the inverse emulsion. For instance, the imprint beads can take on the form of beads or spheres depending upon the conditions of the inverse emulsion.

The size of the surface or oriented imprint beads prepared by the methods of the present invention can be controlled by factors that are within the knowledge of those of skill in the art of inverse emulsions. For instance, the size of the surface or oriented imprint beads is affected by the choice of solvents, optional surfactants and dispersants, mixing temperature, agitation and other factors. Typically, the imprint beads will range in size from about 0.1 μm to about 1000 μm, and may be even larger. Beads on the smaller side will typically have diameters in the range of about 0.5 μm, 1 μm, 2 μm, 10 μm or 15–16 μm. Beads on the larger side will typically have diameters in the range of about 100 μm, 200 μm, 300 μm, 400 μm, 500 μm or 600 μm. In many embodiments, the imprint beads will have diameters between about 0.1–1 μm and about 100, 200, 300, 400, 500 or 600 μm, between about 0.5–2 μm and about 100, 200, 300, 400 or 600 μm, between about 2 μm and about 20–30 μm, between about 0.5–2 μm and about 15, 16 or 20 μm and between about 100 μm and 600 μm. In addition, the size of the surface or oriented beads can be further controlled by the use of sieves as is known to those of skill in the art. For some applications it is preferable that a collection of imprint beads of the invention have a narrow range of size distribution. For example, 90% of the imprint beads of the collection may have a size within about 40% of the average diameter of the beads within the collection. Polymerization conditions are known in the art which produce beads of substantially monodisperse size distribution. These methods may be readily adapted to produce monodisperse imprint beads of the invention.

5.3 Targets

The imprint beads of the present invention can be used to detect, capture, isolate, analyze and/or quantify any target molecule. Target molecules specifically include any species that has a three-dimensional topography that is capable, at least in part, of binding cavities in a matrix material that correspond at least a portion of the three-dimensional topography of the target. Typical examples include, by way of example and not limitation, organic molecules, small molecules, therapeutic molecules, polymers, macromolecules and biological macromolecules. However, targets are not limited to molecular substances, as the imprint beads of the present invention can be used to capture substances as large as viruses and bacteria or even larger objects.

In several important embodiments, target molecules are macromolecules. Macromolecules that can be captured, isolated, detected, analyzed and/or quantified using the imprint compositions of the invention include any type of macromolecule from which a template moiety can be designed and constructed according to the principles taught herein. Virtually any type of macromolecule can be captured, isolated, detected, analyzed and/or quantified using the methods and compositions of the invention. Non-limiting examples include biological polymers such as polypeptides, glycoproteins, polynucleotides and polysaccharides, non-biological polymers such as polyesters, polyethers, polyurethanes, block co-polymers, and other polymers known to those of skill in the art. Non-limiting examples also include biological and non-biological non-polymeric compounds such as antibiotics, steroids, natural products, dyes, etc. Thus, non-limiting examples of the myriad types of macromolecular that may be captured, isolated, detected, analyzed and/or quantified using the methods and compositions of the invention include cytokines, hormones, growth factors, enzymes, cofactors, ligands, receptors, antibodies, carbohydrates, steroids, therapeutics, antibiotics, and even larger structures such as viruses or cells, and other macromolecular targets that will be apparent to those of skill in the art.

5.4 Template Moieties

As discussed above, the imprint compositions of the invention are prepared from a template molecule. The template molecule can be the target molecule to be captured, or it can correspond to the entire structure of the target molecule, or the template molecule can correspond to a portion of the target molecule. A template molecule "corresponds" to the entire structure of the target molecule if it possesses the structural features of the target molecule as described below. Methods of making imprint compositions utilizing templates that correspond to a portion of the target molecule are described in detail in copending application Ser. No. 09/507,300, supra.

The template molecule can possess structural features of a molecule by way of structural identity with the molecule or portion. Alternatively, the template molecule can possess structural features of the molecule or portion by mimicking those structural features of the molecule. The only requirement of the template molecule is that it comprises a three-dimensional structure that is similar enough to the structure of the molecule or portion so that the molecule or portion specifically fits within a cavity formed by the template molecule.

A template molecule can correspond to a target molecule without being identical to the target molecule. Those of skill in the art will recognize that a template molecule need not have exact structural identity with the target molecule in order to "correspond" to it. Often, a template molecule may incorporate topographic substitutions. A substitution is "topographic" if the topography of the template molecule creates a cavity that binds the corresponding target molecule. Preferably, a template with a topographic substitution creates an imprint that specifically binds the corresponding target molecule. Template moieties comprising topographic substitutions, and that therefore do not correspond identically to the target molecule, are said to correspond substantially to the target molecule. Thus, unless specifically indicated otherwise, as used herein, the expression "corresponds to" is intended to encompass those situations where a template molecule corresponds identically or substantially to a molecule of interest. The correspondence between the topography of the template molecule and the topography of the target molecule should be close enough so that the target molecule fits specifically within an imprint or a cavity formed by the template molecule.

The closeness of the correspondence between the template molecule and the molecule of interest will depend upon the desired degree of specificity between the imprint and the target molecule. Template moieties that correspond identically to the target molecule are expected to exhibit the highest degree of specificity for the molecule. Thus, the closeness of correspondence will depend upon the complexity of the separation, and will be apparent to those of skill in the art.

Template moieties that correspond to an entire molecule or to a portion of a molecule can be prepared according to known principles. In many instances the template molecule is simply the same molecule as the target molecule. In other instances the template molecule can be a derivative of the target molecule. For instance, the target molecule can be modified so that it can be linked to a tail molecule as described below. Alternatively, the template molecule can mimic the topography of the target molecule.

Those of skill in the art will also recognize that in many instances compounds that mimic the structures of other compounds are known. For example, peptidomimetic compounds mimic the structures of peptides. The template molecule may comprise, in whole, or in part, such mimetic structures. Mimetic compounds that can be used to create template moieties, as well as their use to create template moieties, will be apparent to those of skill in the art. All that is required is that the three dimensional surface of the mimetic template compound have a three dimensional surface with sufficient correspondence to the surface of the mimicked molecule to create a cavity that specifically fits the molecule.

If the target molecule is a macromolecule, a preferred template molecule corresponds to a portion of the macromolecule of interest. A template molecule "corresponds" to a portion of the macromolecule if it possesses the structural features of that portion of the macromolecule and substantially no other structural features of the macromolecule outside that portion. The template molecule can possess structural features of the macromolecule by way of structural identity with the portion of the macromolecule. Alternatively, the template molecule can possess structural features of the portion of the macromolecule by approximating or mimicking the structure of at least one structural moiety of the portion of the macromolecule.

Those of skill in the art will recognize that a template molecule need not have exact structural identity with the portion of the macromolecule in order to correspond to that portion. Often, a template molecule may incorporate topographic substitutions. A substitution is "topographic" if the topography of the template molecule creates a cavity that binds or captures the corresponding portion of the macromolecule. Preferably, a template including a topographic substitution creates an imprint that specifically binds the corresponding portion of the target macromolecule. Template molecules comprising topographic substitutions, and that therefore do not correspond identically to a portion of the macromolecule, are said to correspond substantially to the macromolecule. Thus, unless specifically indicated otherwise, as used herein, the expression "corresponds to" is intended to encompass those situations where a template molecule corresponds identically or substantially to a portion of the macromolecule of interest.

When constructing a template molecule that does corresponds substantially to a portion of the macromolecule, the template molecule should be topographically of a size that is similar to or larger than the portion of the macromolecule, so that the macromolecule can fit within or bind the imprint cavity created by the template molecule. For example, since Phe and Tyr have side chains of similar structure, and the Phe side chain can be viewed as a "sub-set" of the Tyr side chain, a template molecule having a Phe or Tyr corresponds to a macromolecule Phe. Similarly, a template molecule Cys, Ser or Thr corresponds to a macromolecule Ser. Thus, Tyr is a topographic substitution of Phe, and Ser and Thr are topographic substitutions of Cys. For the twenty genetically encoded amino acids, preferred corresponding template amino acids are as follows:

TABLE OF CORRESPONDENCE

| | Macromolecule | Template |
|---|---|---|
| Aliphatic | Ala | Ala, Val, Leu, Ile |
| | Val | Val |
| | Leu | Leu |
| | Ile | Ile |
| Non Polar | Gly | Gly, Ala |
| | Pro | Pro |
| | Cys | Cys, Ser, Thr |
| | Met | Met, Lys, Arg |
| Aromatic | His | His, Trp |
| | Phe | Phe, Tyr |
| | Tyr | Tyr |
| | Trp | Trp |
| Polar | Asn | Asn, Gln |
| | Gln | Gln |
| | Ser | Ser, Cys, Thr |
| | Thr | Thr |
| Charged | Lys | Lys |
| | Arg | Arg |
| | Asp | Asp, Glu |
| | Glu | Glu |

Non-encoded amino acids and/or amino acid analogues that correspond to portions of a polypeptide macromolecule will be apparent to those of skill in the art. In addition, for other types of macromolecules, those of skill in the art will recognize that template molecules can be selected or prepared with topographic substitutions according to the principles discussed above for polypeptide macromolecules. For example, an oligonucleotide macromolecule adenine can be topographically substituted with 7-diazadenine; a macromolecule guanine with 7-diazaguanine; a macromolecule cytosine with 5-methylcytosine, etc. Specific topographic substitutions will depend upon the specific macromolecule and will be apparent to those of skill in the art.

The closeness of the correspondence between the template molecule and the macromolecule of interest will depend upon the desired degree of specificity between the imprint and the target macromolecule. Template molecules that correspond identically to a portion of a macromolecule are expected to exhibit the highest degree of specificity for the macromolecule. Thus, the closeness of correspondence will depend upon, among other factors, the particular application and the complexity of the sample, and will be apparent to those of skill in the art. Preferably, the template molecule will correspond identically to a portion of the macromolecule to be captured.

It has been discovered that the presence of reactive groups such as sulfhydryl groups in template molecules can be disadvantageous for the preparation of molecular imprints. Nevertheless, the imprint compositions of the present invention can be prepared to capture macromolecules that contain such reactive groups. The imprint compositions of the present invention can be prepared so efficiently and inexpensively that a number of techniques can be applied to such macromolecules. To avoid including such reactive groups, a template can be designed that corresponds to a portion of the macromolecule that does not contain the reactive group. However, if a portion of the macromolecule is selected that includes a reactive group, the template molecule can be designed to include a topographic substitution for the reactive group. In particular, macromolecular Cys residues can be substituted to Ser or α-aminobutyrate residues in the template molecule. Alternatively, reagents can be used to reduce or block the reactive groups of the macromolecule and of the corresponding template molecule. Such reagents are known to those of skill in the art. For example, any template Cys residue can be reduced with dithiothreitol or β-mercaptoethanol and blocked with reagents that prevent the formation of inter molecular or intramolecular disulfide bridges such as N-ethylmaleimide, iodoacetic acid or other reagents known to those of skill in the art (the SH groups may interfere with the polymerization reaction). When the template molecules are "blocked" in this fashion, the reactive groups in the macromolecule to be captured are preferably blocked with the same reagent, as a higher degree of specificity during capture will be achieved. For example, to capture a polypeptide macromolecule which includes disulfide bridges with a molecular imprint prepared with a template molecule in which the Cys residues are blocked, the disulfide bridges of the macromolecule should be reduced prior to, or concomitant with, contacting the macromolecule with the molecular imprint. Preferably, the sulfhydryl groups of the reduced Cys residues will be further blocked with the same reagent used to block the template Cys residues.

A detailed description of template moieties that correspond to portions of macromolecules are described in detail in copending application Ser. No. 09/507,300, supra.

5.5 Template Moieties for Preparing Imprints Useful for Capturing Novel Macromolecules Template moieties that comprise the structure of a known molecule or that correspond to a portion of a known molecule are most useful for capturing known molecules. However, in another important embodiment, the present invention is also useful for capturing, isolating, detecting, analyzing, quantifying and/or identifying novel molecules. In this embodiment, the template moiety useful for preparing imprints which can capture novel molecules, even those for which no structural information is known.

In this embodiment, the template moiety can be any molecule that might be useful for capturing a novel molecule. For instance, the template moiety can be a small molecule that is useful for preparing imprint beads that can be used to capture novel molecules of similar structure. The template moiety can be selected from a combinatorial library, or any other library of molecules known to those of skill in the art. Any template moiety that can be linked to tail molecule to form a conjugate molecule, as described below, is useful for preparing imprint beads of the present invention.

In particular, template moieties of this embodiment are useful for preparing imprints that can capture a novel macromolecule. A novel macromolecule is a macromolecule for which limited or no structural or functional information is available. If any structural information is available, a molecular imprint can be prepared using a template moiety that corresponds to the portion of the available structural information as described above. The template moiety can also correspond to all of the available structural information. When no structural information is known about a macromolecule, but it is known to be functionally related to a known macromolecule, the template moiety can correspond to a portion of a macromolecule having similar function, the template moiety can correspond to a portion of a macromolecule with similar function, or the template moiety can correspond to a consensus sequence of a family of macromolecules with similar function. In addition, for any novel macromolecule, even one for which no structural or functional information is available, a molecular imprint of a template moiety with a random structure might be able to capture the novel macromolecule. For example, an as yet unidentified macromolecule can be captured, isolated, detected, analyzed and identified from a complex sample with such a molecular imprint. Template moieties appropriate for creating imprint beads that can capture novel macromolecules are described in detail in copending application Ser. No. 09/507,300, supra.

5.6 Conjugate Molecules

The conjugate molecule comprises a tail moiety and a template moiety. The conjugate molecule partitions to an interface of a multiple-phase system because of its amphipathic character. Template moieties constitute template molecules, which are described in detail above, that are to be imprinted.

Since the structure of the template moiety is determined by the structure of the target molecule, the amphipathic character of the conjugate molecule is established by careful selection of the tail moiety based on the properties of the template moiety. Generally, referring to FIG. 3B, the template moiety is soluble in water phase 46 which comprises matrix material 42. The tail moiety should be chosen so that the conjugate molecule partitions to an interface of phases 46 and 48. Preferably, the tail moiety is chosen so that it is soluble in phase 48.

Non-limiting examples of suitable hydrophobic tail molecule moieties include straight-chain, branched, cyclic and polycyclic hydrocarbons, cyclic and polycyclic aryls, fatty acids such as palmitic acid, lipids, phospholipids, steroids, cholesterol and derivatives thereof, hydrophobic polypeptides, etc. The necessary degree of hydrophobicity will depend upon a variety of factors, including, among others, the solvents used to create the two-phase system and the hydrophilicity of the template moiety, and will be apparent to those of skill in the art.

In a non-limiting example, template moiety 34 can be a peptide. The hydrophobicity of template moiety 34 can be determined according to techniques known to those of skill in the art such (Eisenberg, 1984, Ann. Rev. Biochem. 53:595–623; Eisenberg, 1984, J. Mol. Biol. 179:125–142; Eisenberg et al., 1982, Nature 299:371–374; Kyte and Doolittle, 1982, J. Mol. Biol. 157:105–32). The hydrophobicity of the tail moiety conjugated to a peptide template moiety should allow the resulting conjugate molecule to partition to an interface of the appropriate solvent system.

The template moiety is covalently linked to the tail moiety by any method known to those of skill in the art either directly or by way of an optional linker. The actual linkage will depend upon the identities of the template moiety and the tail moiety and will be apparent to those of skill in the art. For example, a hydrophilic peptide template moiety and a hydrophobic peptide tail moiety can be linked at their respective N- and C-termini to form an amide linkage. Alternatively, the template moiety and the tail moiety can be linked by a linker 35. Linker 35 can be any molecule used by those of skill in the art to link two other molecules. The linker molecule may be rigid, semi-rigid or flexible, hydrophilic or hydrophobic, long or short, etc. A plethora of linkers suitable for linking two or more moieties are known in the art. Any of these linkers can be used to link the two moieties. The actual choice of linker molecule will depend upon, among other things, the nature of the template moiety or the tail moiety, the length vs. rigidity of the linker, etc., and will be apparent to those of skill in the art. Other suitable linkers 35 will be apparent to those of skill in the art. For example, bifunctional reagents are known to those of skill in the art and are commercially available. The linker molecule can form a covalent linkage between the template moiety and the tail moiety, or the linkage can be non-covalent.

The linkage between the template moiety and the tail moiety can be optionally cleavable. Cleavable linkages are known to those of skill in the art and include linkages that can be cleaved with chemicals, enzymes, or electromagnetic radiation. If the linkage can be cleaved with electromagnetic radiation and the transition of matrix material 42 can also be induced by electromagnetic radiation, the wavelength of the radiation that cleaves the linkage should be compatible with the wavelength of the radiation that induces the transition of the matrix material.

5.7 Imprint Beads

In another aspect, the invention provides imprint bead compositions comprising a matrix material having a cavity of a template moiety imprinted thereon. The imprint beads are prepared by the methods described in detail above. The cavities are oriented and localized at or near the surface of the matrix material. The cavities have topographies that correspond to the topography of the template moiety. The template moiety is designed or selected to generate cavities that correspond in topography to a target molecule. The imprint bead can be used to specifically capture target molecules which bind the cavities. A target molecule "binds" a cavity if it becomes entrapped or immobilized within the cavity in a manner such that it is specifically captured from a composition comprising it.

In an imprint bead of the invention, a higher concentration of imprint cavities are localized at or near the surface of the matrix material, relative to the interior of the bead. In many instances, a substantially higher concentration of cavities are localized at or near the surface. By "substantially higher concertation" is meant that the local concentration of template in a volume element near the surface of the bead is on the order of about 20%, about 50%, about 100%, about 400% or about 1000%, or even higher, than the concentration of the template in a similar volume element in the interior of the bead. An imprint bead may have substantially all, or even all of its cavities localized at or near its surface.

The imprint cavities are also oriented with respect to the surface of the matrix material. In many instances, substantially all, or even all, of the imprint cavities localized at or near the surface of the bead are oriented. Two imprint cavities of the same or similar template moieties are "oriented" if they have a similar or identical spatial relationship to the surface of the matrix material. For example, two imprint cavities of peptides, even peptides of different primary structures, are oriented if the portions of the cavities that correspond to the amino termini of the peptides are, for instance, closer to the surface of the matrix material than the portions that correspond to the carboxy termini, or vice versa. Two imprint cavities of single-stranded polynucleotides are oriented if the portions of the cavities that correspond to the 5' ends of the polynucleotides are, for instance, closer to the surface of matrix material than the portions that correspond to the 3' ends, or vice versa. Two imprint cavities of amphipathic molecules are oriented if the portions of the cavities that correspond, for instance, to the hydrophilic portion of the molecules are closer to the surface of the matrix material than the portions that correspond to their hydrophobic portions, or vice versa. One of skill in the art will recognize that any two imprint cavities of similar template moieties can be oriented within a matrix material.

Figure 1:
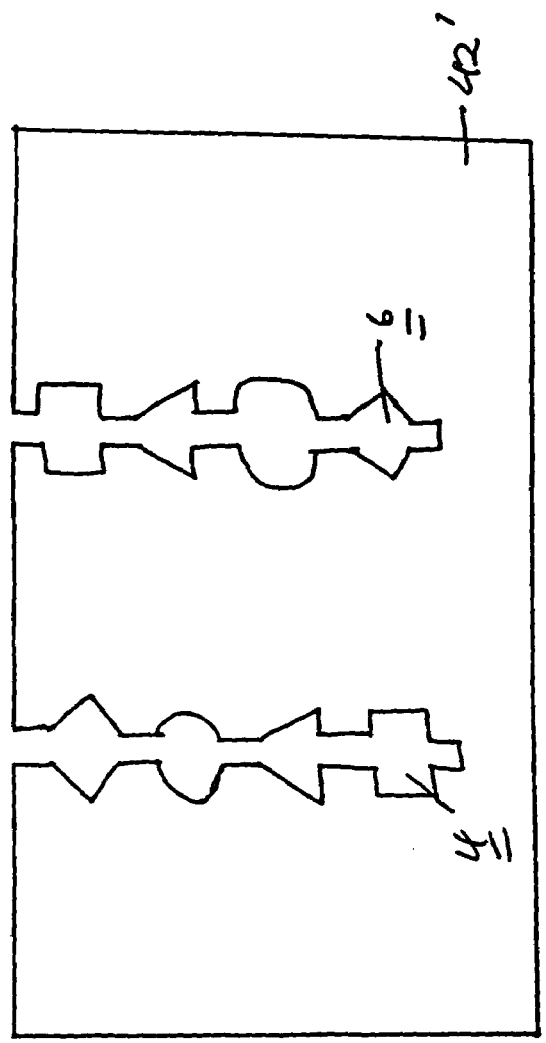
Figure 1:
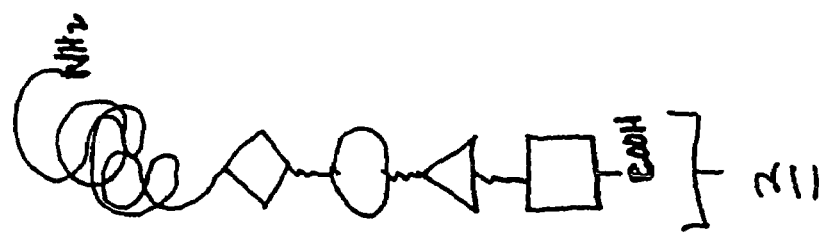
Figure 2:
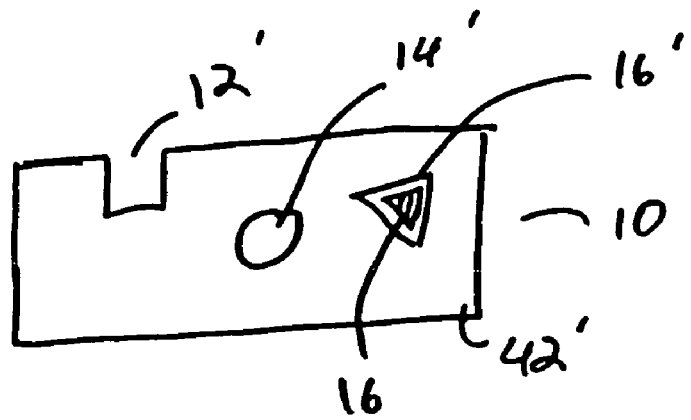
Figure 2:
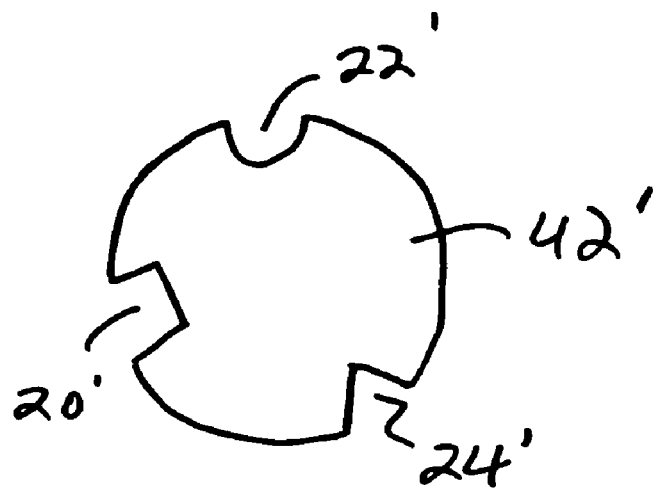

Imprint beads of the present invention are superior to conventional molecular imprints because the cavities of imprint beads are advantageously distributed and/or oriented at the surface of the imprint. As illustrated in FIG. 2, conventional imprint 10 has cavities 12', 14' and 16' distributed throughout matrix material 42'. Some of the cavities such as 12' might be localized at the surface of matrix material 42', but the majority of cavities such as 14' are not surface-accessible. Some cavities such as 16' may even contain internally trapped template moieties such as 16. In contrast, imprint bead 18 has cavities 20', 22' and 24' oriented and localized at or near the surface of the matrix material. Cavities 20', 22' and 24' contain no trapped template moieties are accessible and oriented at the surface of the imprint.

5.8 Arrays of Imprint Beads

The present invention also provides arrays of imprint bead compositions. The arrays are comprised of a plurality of individual imprint bead compositions arranged in an array or pattern. The arrays may be one-dimensional, two-dimensional or three-dimensional. For instance, a one-dimensional array can be prepared by introducing the beads into a capillary tube. A two-dimensional array can be prepared, for example, by distributing the beads into the wells of a microtiter plate and/or by affixing the individual beads onto a substrate.

Figure 4A:
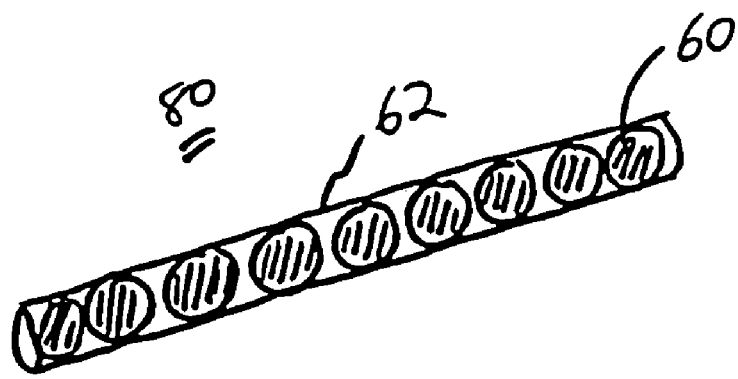
FIG. 4 illustrates one-dimensional (4A) and two-dimensional (4B) arrays of imprint beads distributed on a substrate.
Figure 4B:
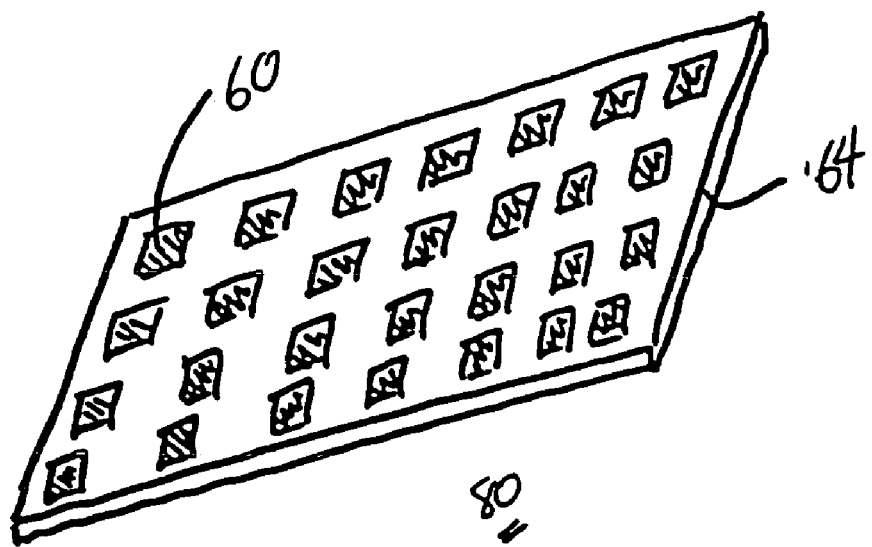

For example, referring to FIG. 4A, the array can be an ordered pattern of individual beads 60 where each bead 60 is an imprint composition of the invention. As illustrated in FIG. 4, the individual beads 60 may be disposed within a housing 62. Housing 62 can serve the dual purpose of retaining the ordering of individual beads 60 and providing a structure through which the sample may be flowed. The ends of the capillary tube may be optionally plugged with, for example, glass wool, a frit, or other porous materials to hold the beads in the tube during sample flow. Alternatively, individual beads 60 could be distributed, either singly or in pluralities, amongst the wells of, for example, a microtiter plate, or affixed to the surface of a substrate, such as a glass plate, plastic sheet or film, etc.

As illustrated by the above examples, a key feature of the arrays of the invention is the ability to correlate the identity of a particular imprint with its relative position within the array. Thus, in an array of beads in the wells of a microtiter plate, the identity of a particular imprint 60 is identifiable by its xy-coordinates within the array. In the array illustrated in FIG. 4, the identity of a particular imprint 60 is identifiable by its x-coordinate within the array. This feature is particularly useful for detecting, capturing, isolating, analyzing and/or quantifying pluralities of molecules in complex samples, as will be discussed in more detail, below.

In the arrays of the invention, each array element (i.e., each set of array coordinates) may be unique, i.e., each address in the array may contain an imprint of a different template moiety, or alternatively, the array may comprise redundancies. Moreover, while in many instances each array element will comprise imprint cavities of a single template moiety, one or more of the array elements may comprise imprint cavities of 2 or more different template moieties.

The number of elements comprising the array can vary over a wide range, from as few as 2 to as many as 10, $10^2$, $10^3$, $10^4$, $10^5$, $10^6$ or even more, and is limited only by the ability to make an array having the desired complexity, as will be described in more detail, below.

A spatially identifiable array of imprint beads is particularly useful when an array of imprint beads of template moieties is used to screen a complex mixture in order to isolate novel molecules. Structural information about any captured novel molecule can be deduced from the position at which it binds the array. The portion of the captured novel molecule must have a structure that corresponds to the structure of the template moiety that was used to create the imprint at that position in the array. If the captured, novel molecule is a protein and the imprint beads is an imprint of a peptide template moiety, then a portion of the amino acid sequence of the captured protein might even be identical to the amino acid sequence of the peptide template moiety.

5.9 Methods of Capturing Target Molecules

Also within the scope of the present invention are methods of using imprint beads to capture target molecules. Imprint beads useful for methods of capturing target molecules can be prepared as described above. To capture a molecule, the molecule or a mixture comprising the molecule is contacted with the molecular imprint under conditions in which the molecule binds the imprint.

Preferably, the conditions for contacting the target molecule with the imprint are similar to or identical to the conditions under which the imprint was formed. The choice of conditions depends on the target molecule and the template moiety. When the target molecule is a protein and the template moiety corresponds to sequence of amino acids of the protein, the preferred capture conditions are often denaturing. However, when a template moiety corresponds to a large fragment of a protein, such as a pepsin fragment of an immunoglobulin, or when a template corresponds to a domain exposed on the surface of a target protein, then native imprinting and capture conditions will often yield superior results. When the target molecule is a double-stranded polynucleotide, the preferred capture conditions are native conditions that allow the target molecule to maintain its native structure. When the target molecule is a single-stranded polynucleotide, the capture conditions may be native or denaturing conditions. One of skill in the art will recognize whether native or denaturing conditions are appropriate. In situations where the choice of imprinting and capture conditions is not clear, the molecular imprint compositions of the present invention can be prepared so efficiently and inexpensively that a series of conditions can be assayed to determine the ideal conditions.

The exact conditions to retain a native or denatured structure are well-known and will be apparent to those of skill in the art. For instance, denaturing conditions for polypeptides can include SDS, urea, guanidine, or any other protein denaturant known to those of skill in the art. Denaturing conditions for polynucleotides can include high temperature, formamide, high ionic strength, and other conditions known to those of skill in the art.

For capture, the imprint bead compositions may be disposed within a housing to create a chromatography column, or used batch-wise. The imprint bead compositions can also be disposed in a capillary tube. Imprint bead compositions in a capillary tube can be used to capture the same target molecule. In addition, in an advantageous embodiment, imprint bead compositions in a capillary tube can be used to capture different target molecules. If the identity of each imprint bead composition in the capillary tube is known, the identity of a bound target molecule can then be determined by the position of its binding in the capillary tube.

A plurality of target molecules can be captured simultaneously by contacting the target molecules with an array of the invention. The amount of a target molecule in a sample can be quantified by capturing the target molecule with a molecular imprint and determining the amount of the target molecule captured by the imprint. Techniques for detecting a captured molecule or quantifying the amount of a captured molecule include infrared spectroscopy, UV spectroscopy, visible spectroscopy, surface acoustic wave devices, refractive index, evanescent wave sensors, bulk acoustic wave devices, capacitance measurements, radioimmunoassay measurements, radiolabeling, chemiluminescence measurements, SYPRO dyes (Steinberg et al., 1996, *Anal Biochem.* 239:223–37; Molecular Probes, Eugene, Oreg.), Lamb-wave measurements, fluorescence measurements, fluorescent particles, Wilhelmy balance, chemiresistor measurements, electrochemical sensors, enzyme-s linked immunosorbent assay, resistance, capacitance, acoustic wave, surface plasmon resonance, scanning tunneling microscopy, atomic force microscopy, scanning electron microscopy, rolling circle amplification, quantum dots and other techniques known to those of skill in the art for detecting or quantifying molecules such as those described in U.S. Pat. Nos. 5,306,644; 5,313,264; 5,955,729; and 5,976,466.

In one representative embodiment, captured molecules can be detected or quantified by measuring the change in ultraviolet absorbance of the array of imprints before and after capture. Alternatively, the change in resistance or capacitance of the array before and after capture can be used to detect captured molecules or quantify the amount of captured molecules. In another embodiment, a plurality of macromolecules can be radioactively labeled by covalent modification with a radioactive reagent or by synthesizing the macromolecules from radioactively labeled precursors. Captured molecules can then be detected or quantified by counting radioactive emissions from the array by techniques well-known to those of skill in the art.

The relative amounts of a plurality of different target molecules can be quantified by capturing the plurality of target molecules and quantifying the amount of each target molecule of the plurality bound to the imprints. In a preferred embodiment, the identity of each imprint is determinable from its relative position within the array. An array of imprints wherein the identity of each imprint is determinable can be prepared from an array of template moieties wherein the identity of each template moiety is determinable from its relative position within the array. Methods of preparing such arrays of template moieties are known to those of skill in the art.

An array of imprint beads according to the present invention is useful for determining the relative amounts of target molecules from a complex biological source. This embodiment of the invention specifically encompasses the evaluation of an expression profile of a cell. In this embodiment, the complex mixture of target molecules comprises a plurality of polypeptides from a cell. An array of imprints is prepared using template moieties that correspond to portions of the polypeptides of the plurality. The plurality of polypeptides is contacted with the array of imprints. The absolute or relative amount of each polypeptide captured by the array of imprints is determined by a method of quantifying polypeptides known to those of skill in the art. For example, the cell that is the source of the plurality of polypeptides can be grown in the presence of radioactively labeled amino acids. The amount of each polypeptide bound by the array can then be determined by scintillation counting or by photographic exposure and densitometry. Alternatively, if antibodies are available for the polypeptides of the plurality, the amount of the polypeptides bound by the array of imprints can be determined by ELISA methods or other methods known to those of skill in the art. If each imprint of the array is on a discrete matrix, then the amount of each bound polypeptide can be determined directly by a protein assay known to those of skill in the art such as the assay described in Lowry et al., 1951, *J. Biol. Chem.* 193: 265–220, or the assay described in Bradford, 1976 *Anal. Biochem.* 72: 248–254. The expression profile of the polypeptides of the plurality can be derived from the relative amounts of each polypeptide of the plurality that is bound by the array of imprints.

A captured target molecule can be analyzed by any of the techniques discussed above for detecting or quantifying captured target molecule. For example, post-translational modification of a captured target macromolecule can be analyzed by, for instance, an ELISA method. In particular, phosphorylation of a captured target macromolecule can be analyzed with antibodies specific for phosphotyrosine or phosphoserine. Glycosylation of a captured target macromolecule can be analyzed with lectins such as concanavalin A or wheat germ agglutinin. Other features of a captured target molecule can be analyzed using any of the techniques described above or any other technique known to those of skill in the art.

A target molecule can be isolated by capturing the target molecule with an imprint bead and then recovering the target molecule from the imprint. The target molecule can be recovered from the imprint by diffusion or by incubation in urea, guanidine, SDS, or other techniques known to those of skill in the art for disrupting macromolecular complexes or for denaturing molecules.

5.10 Methods of Screening Molecules

In another aspect, the present invention is drawn to methods of screening molecules. This aspect of the invention encompasses screening both molecules of determined structure and screening of those of undetermined structure. To screen a plurality of molecules, the plurality is contacted with a plurality imprints. In one embodiment, a substrate comprises a plurality of imprints. In another embodiment, a plurality of substrates comprises a plurality of imprints.

At least one imprint of the plurality is an imprint bead of a template moiety that does not necessarily correspond to any portion of a known molecule as defined above. If the molecules to be screened are polypeptides, the template moiety should be a peptide, a polysaccharide or a fatty acid, as appropriate. If the molecules to be screened are polynucleotides, the template moiety should be a polynucleotide. If the molecules to be screened are polysaccharides, the template moiety should be a polysaccharide. If the molecules to be screened are a mixture of different classes of molecules, the plurality of imprints can comprise imprints of template moieties of the corresponding classes.

A sample containing a plurality of molecules is contacted with the plurality of imprints. If any molecule of the sample contains a structure that corresponds sufficiently to the structure of the template moiety, the molecule will be captured by the plurality of imprints. Any molecules captured can be quantified or recovered from the imprint. Since template moieties can have structures that do not correspond to any portion of the structure of any known molecule, the present method of screening can be used to capture, isolate, and identify novel molecules from complex samples.

6. EXAMPLES

6.1 Example 1

Preparation of Conjugate Molecules

To create imprint beads capable of binding the proteins horse heart cytochrome c, alcohol dehydrogenase, bovine serum albumin, creatine kinase and estrogen receptor, five conjugate molecules, each corresponding in structure to the seven carboxy-terminal amino acids of one of the five proteins, were constructed.

For cytochrome c, a template moiety was first designed having the amino acid sequence of the seven carboxy-terminal amino acids of the horse heart cytochrome c polypeptide, LKKATNE. A seven amino acid sequence should be sufficiently unique to provide an imprint bead with specificity for cytochrome c. A peptide with the sequence LKKATNE was synthesized by standard techniques. A conjugate molecule was then prepared with the LKKATNE template moiety. Since LKKATNE is a hydrophilic template moiety (see Kyte & Doolittle (1982), J. Mol. Biol. 157: 105–132), palmitic acid was chosen as a hydrophobic tail molecule. Palmitic acid was linked to the amino-terminus of the LKKATNE via an amide bond to form a palmitoyl-peptide conjugate molecule ("Pal-CytC").

Similarly, palmitic acid was linked to the amino-terminus of a peptide having the amino acid sequence of the seven carboxy-terminal amino acids of alcohol dehydrogenase, YVVDTSK, to form Pal-ADH. Palmitic acid was also linked to the amino-terminus of a peptide having the amino acid sequence of the seven carboxy-terminal amino acids of bovine serum albumin, STQTALA, to form Pal-BSA. Additionally, palmitic acid was linked to the amino-terminus of a peptide having the amino acid sequence of the seven carboxy-terminal amino acids of creatine kinase, DMI-PAQK, to form Pal-CK. Finally, palmitic acid was linked to the amino-terminus of a peptide having the amino acid sequence of the seven carboxy-terminal amino acids of estrogen receptor, SQNPQSQ, to form Pal-ER.

6.2 Example 2

Preparation of Acrylamide Imprint Beads Capable of Binding Cytochrome c.

In this example, we demonstrate the preparation of acrylamide beads capable of binding cytochrome c.

The CytC imprint beads were prepared in an inverse emulsion system with a Pal-CytC conjugate molecule of Example 1 whose structure corresponds to the amino acid sequence of the carboxy-terminus of cytochrome c. The nonionic surfactant Arlacel 83 was used to generate the inverse emulsion. The Pal-CytC conjugate molecule, with a hydrophilic template moiety linked to a hydrophobic tail moiety, was designed to be capable of partitioning to an interface of an inverse emulsion.

The aqueous phase of the inverse emulsion was prepared by combining 1 g acrylamide, 0.17 g N-N'-ethylene bisacrylamide and 4.6 mg Pal-CytC in 5 ml of 4 M urea and 10 mM MES pH 6.0. The organic phase of the inverse emulsion was prepared by dissolving 1.95 g Arlacel 83 (Uniqema) and 15 mg 2,2'-azobisisobutyronitrile in 27.6 g Isopar M (Exxon). The aqueous (5 ml) and organic phases (5 g) were mixed and purged with nitrogen for 10 min at 15° C. The resulting mixture was then emulsified by stirring for 5 min. Polymerization was initiated with ultraviolet light at 365 nm and proceeded at 15° C. for 12 hr under continuous nitrogen flow. A latex comprising water-swollen polymeric beads dispersed in Isopar M was obtained.

The resulting imprint beads were washed with a solution of 4 M urea, 10 mM MES pH 5.0 and 0.35 M SDS overnight. The imprint beads were then washed three times with solutions of 4 M urea and 10 mM MES pH 5.0 to remove the SDS. The washed imprint beads were stored in a solution of 4 M urea and 10 mM MES pH 5.0 (short term) or in Isopar M (long term).

6.3 Example 3

Preparation of Acrylamide Imprint Beads Capable of Binding Alcohol Dehydrogenase In this example, we demonstrate the preparation of acrylamide imprint beads capable of binding alcohol dehydrogenase.

The ADH imprint beads were prepared in an inverse emulsion system with a Pal-ADH conjugate molecule of Example 1 whose structure corresponds to the amino acid sequence of the carboxy-terminus of alcohol dehydrogenase. The nonionic surfactant KLE 3736 was used to generate the inverse emulsion. The Pal-ADH conjugate molecule, with a hydrophilic template moiety linked to a hydrophobic tail moiety, was designed to be capable of partitioning to an interface of an inverse emulsion.

The aqueous phase of the inverse emulsion was prepared by dissolving 1 g acrylamide, 0.17 g N-N'-ethylene bisacrylamide and 5 mg Pal-ADH in 5 ml of 4 M urea and 10 mM MES pH 6.0. The organic phase of the inverse emulsion was prepared by dissolving 0.64 g KLE 3736 (Goldschmidt, AG) and 50 mg 2,2'-azobisisobutyronitrile in 74 g Isopar M (Exxon). The aqueous and organic phases were mixed and purged with nitrogen for 20 min at 18° C. in a 250 ml batch reactor. The resulting mixture was then emulsified by stirring for 5 min. Polymerization was initiated with ultraviolet light at 365 nm and proceeded at 18° C. overnight under continuous nitrogen flow. A latex comprising water-swollen polymeric beads dispersed in ISOPAR M was obtained.

The resulting polymeric beads were washed with Isopar M and a solution of 4 M Urea and 10 mM MES pH 5.0. The conjugate molecule was then eluted with a solution of 4 M urea, 10 mM MES pH 5.0 and 0.35 M SDS overnight. The polymeric beads were then washed three times with solutions of 4 M urea and 10 mM MES pH 5.0 to remove the SDS. The washed polymeric beads were separated on a sintered glass funnel.

6.4 Example 4

Preparation of Acrylamide Imprint Beads Capable of Binding Alcohol Dehydrogenase In this example, we demonstrate the preparation of acrylamide beads capable of binding alcohol dehydrogenase (ADH).

The ADH imprinted beads were prepared in an inverse emulsion system with a Pal-ADH conjugate molecule of Example 1. The nonionic surfactant Arlacel 83 was used to generate the inverse emulsion. The Pal-ADH conjugate molecule, with a hydrophilic template moiety linked to a hydrophobic tail moiety, was designed to be capable of partitioning to an interface of an inverse emulsion.

The aqueous phase of the inverse emulsion was prepared by dissolving 1.5 g acrylamide, 0.5 g N-N'-ethylene bisacrylamide and 5 mg Pal-ADH in 5 ml of 4 M urea and 10 mM MES pH 5.0. The organic phase of the inverse emulsion was prepared by dissolving 0.5 ml Arlacel 83 (Uniqema) and 17 mg 2,2'-azobisisobutyronitrile in 10 ml Isopar M (Exxon). The aqueous and organic phases were mixed and purged with nitrogen. The resulting mixture was then emulsified by vortexing. Polymerization was initiated with ultraviolet light at 365 nm and proceeded at 15° C. for 12 hr under continuous nitrogen flow. A latex comprising water-swollen polymeric beads dispersed in Isopar M was obtained.

The resulting imprint beads were washed with a solution of 4 M urea, 10 mM MES pH 5.0 and 0.35 M SDS. The imprint beads were then washed three times with solutions of 4 M urea and 10 mM MES pH 5.0 to remove the SDS. The washed imprint beads were stored in a solution of 4 M urea and 10 mM MES pH 5.0 (short term) or in Isopar M (long term).

6.5 Example 5

Specific Binding of Alcohol Dehydrogenase by Imprint Beads

In this example, we demonstrate that the ADH imprinted beads of Example 4 specifically bind alcohol dehydrogenase.

Figure 5:
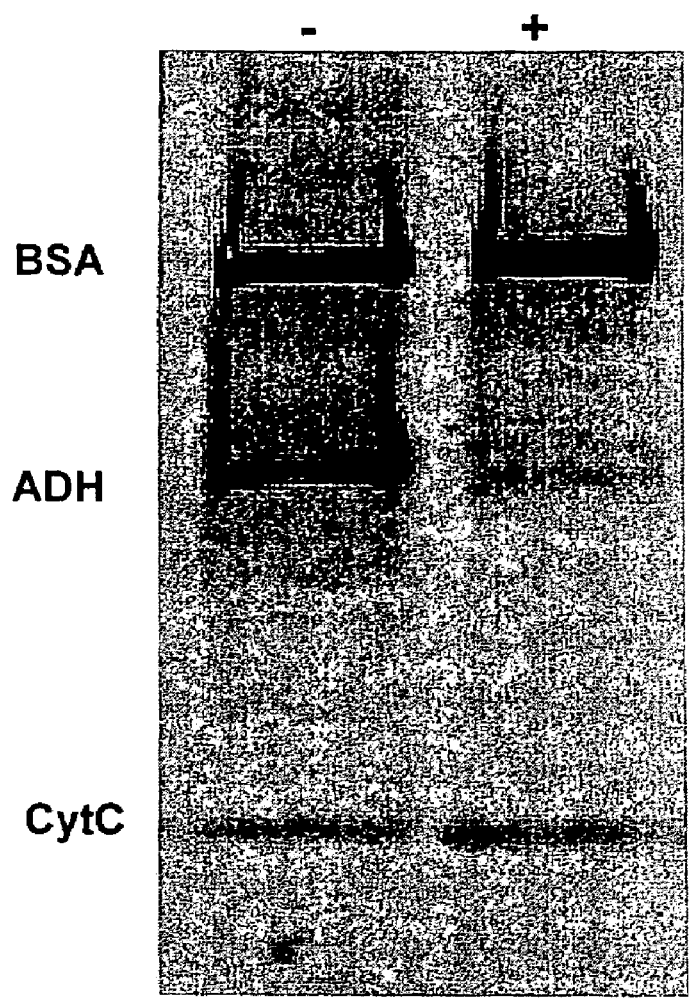
FIG. 5 shows a silver stained gel of a mixture of bovine serum albumin (BSA), alcohol dehydrogenase (ADH) and cytochrome C (CytC) exposed to beads of the invention imprinted with a seven amino acid peptide corresponding to the C-terminus of ADH (+) and non-imprinted control beads (−). The ADH imprinted beads specifically capture the alcohol dehydrogenase from solution.

Non-imprinted control beads were prepared as described in Example 4, except that the Pal-ADH conjugate molecule was excluded. The ADH imprinted beads of Example 4 and the non-imprinted beads were separately incubated with a mixture of 3 proteins (bovine serum albumin(BSA), ADH and CytC) at room temperature for 3 hours in 10 mM MES, pH 5.0, containing 4 M urea. The supernatant was removed from the beads and analyzed using SDS-PAGE and silver stain. FIG. 5 shows a silver stained gel of the resulting supernatants. The ADH imprinted beads (+) specifically capture the alcohol dehydrogenase from solution, whereas the non-imprinted control beads (−) do not.

To demonstrate that the ADH imprinted beads were capable of specifically capturing alcohol dehydrogenase from a complex mixture, the beads of Example 4 were incubated at room temperature with a cell lysate spiked with 1% alcohol dehydrogenase in 10 mM MES, pH 5.0, containing 4 M urea. The beads were separated from the supernatant and the protein bound to the beads were eluted with sample buffer (125 mM Tris-HCl, pH 6.8, 5% v:v 2-mercaptoethanol, 10% v:v glycerol, 2.5% w:v SDS, 0.05% w:v bromophenol blue). The eluted proteins were analyzed using SDS-PAGE and silver stain (FIG. 6). Lane 1 is the cell lysate spiked with alcohol dehydrogenase presented to the beads. Lane 2 is the protein eluted from the ADH imprinted beads. Thus the ADH imprinted beads specifically capture alcohol dehydrogenase from a complex mixture.

6.6 Example 6

Preparation of Acrylamide Imprint Beads Capable of Binding Creatine Kinase

In this example, we demonstrate the preparation of acrylamide beads capable of binding creatine kinase.

The creatine kinase imprint beads were prepared in an inverse emulsion system with a Pal-CK conjugate molecule of Example 1 whose structure corresponds to the amino acid sequence of the carboxy-terminus of creatine kinase. The nonionic surfactant Alracel 83 was used to generate the inverse emulsion. The Pal-CK conjugate molecule, with a hydrophilic template moiety linked to a hydrophobic tail moiety, was designed to be capable of partitioning to an interface of an inverse emulsion.

The aqueous phase of the inverse emulsion was prepared by dissolving 1 g acrylamide, 0.17 g N-N'-ethylene bisacrylamide and 4.2 mg Pal-CK in 5 ml of 4 M urea and 10 mM MES pH 6.0. The organic phase of the inverse emulsion was prepared by dissolving 1.95 g Arlacel 83 (Uniqema) and 15 mg 2,2'-azobisisobutyronitrile in 27.6 g Isopar M (Exxon). The aqueous (5 ml) and organic phases (5 g) were mixed and purged with nitrogen for 10 min at 15° C. The resulting mixture was then emulsified by stirring for 5 min. Polymerization was initiated with ultraviolet light at 365 nm and proceeded at 15° C. for 12 hr under continuous nitrogen flow. A latex comprising water-swollen polymeric beads dispersed in Isopar M was obtained.

The resulting imprint beads were washed with a solution of 4 M urea, 10 mM MES pH 5.0 and 0.35 M SDS overnight. The imprint beads were then washed three times with solutions of 4 M urea and 10 mM MES pH 5.0 to remove the SDS. The washed imprint beads were stored in a solution of 4 M urea and 10 mM MES pH 5.0 (short term) or in Isopar M (long term).

6.7 Example 7

Preparation of Acrylamide Imprint Beads Capable of Binding Bovine Serum Albumin In this example, we demonstrate the preparation of acrylamide beads capable of binding bovine serum albumin.

The bovine serum albumin imprint beads were prepared in an inverse emulsion system with a Pal-BSA conjugate molecule of Example 1 whose structure corresponds to the amino acid sequence of the carboxy-terminus of bovine serum albumin. The nonionic surfactant Alracel 83 was used to generate the inverse emulsion. The Pal-BSA conjugate molecule, with a hydrophilic template moiety linked to a hydrophobic tail moiety, was designed to be capable of partitioning to an interface of an inverse emulsion.

The aqueous phase of the inverse emulsion was prepared by dissolving 1 g acrylamide, 0.17 g N-N'-ethylene bisacrylamide and 3.7 mg Pal-BSA in 5 ml of 4 M urea and 10 mM MES pH 6.0. The organic phase of the inverse emulsion was prepared by dissolving 1.95 g Arlacel 83 (Inigema) and 15 mg 2,2'-azobisisobutyronitrile in 27.6 g Isopar M (Exxon). The aqueous (5 ml) and organic phases (5 g) were mixed and purged with nitrogen for 10 min at 15° C. The resulting mixture was then emulsified by stirring for 5 min. Polymerization was initiated with ultraviolet light at 365 nm and proceeded at 15° C. for 12 hr under continuous nitrogen flow. A latex comprising water-swollen polymeric beads dispersed in Isopar M was obtained.

The resulting imprint beads were washed with a solution of 4 M urea, 10 mM MES pH 5.0 and 0.35 M SDS overnight. The imprint beads were then washed three times with solutions of 4 M urea and 10 mM MES pH 5.0 to remove the SDS. The washed imprint beads were stored in a solution of 4 M urea and 10 mM MES pH 5.0 (short term) or in Isopar M (long term).

6.8 Example 8

Preparation of Acrylamide Imprint Beads Capable of Binding Estrogen Receptor In this example, we demonstrate the preparation of acrylamide beads capable of binding estrogen receptor.

The estrogen receptor imprint beads were prepared in an inverse emulsion system with a Pal-ER conjugate molecule of Example 1. The nonionic surfactant Arlacel 83 was used to generate the inverse emulsion. The Pal-ER conjugate molecule, with a hydrophilic template moiety linked to a hydrophobic tail moiety, was designed to be capable of partitioning to an interface of an inverse emulsion.

The aqueous phase of the inverse emulsion was prepared by dissolving 1.5 g acrylamide, 0.5 g N-N'-ethylene bisacrylamide and 5.0 mg Pal-ER in 5 ml of 4 M urea and 10 mM MES pH 5.0. The organic phase of the inverse emulsion was prepared by dissolving 0.5 ml Arlacel 83 (Uniqema) in 10 ml Isopar M (Exxon). The aqueous and organic phases were combined and vortex-mixed to create the inverse emulsion. The emulsion was transferred into a jacketed mini reactor with a stir bar rotating at maximum velocity and purged with nitrogen. 100 µL of 1.26% (w:w) cumene hydroperoxide in Isopar M was added to the reactor followed by 100 µl of 1% (w:w) sodium metabisulfite in water over a five minute period. Polymerization was allowed to proceed overnight. A latex comprising water-swollen polymeric beads dispersed in Isopar M was obtained.

6.9 Example 9

Specific Binding of Estrogen Receptor by Imprint Beads

In this example, we demonstrate that the imprint beads of Example 8 specifically bind estrogen receptor The imprinted beads of Example 8 were incubated with a estrogen receptor in the presence or absence of a competing peptide. ER imprinted beads were incubated with (a) estrogen receptor alone, or (b) with a mixture of estrogen receptor and 100-fold or 500-fold molar excess of estrogen receptor peptide, SQNPQSQ, or (c) with a mixture of estrogen receptor and 100-fold or 500-fold excess of an unrelated peptide, STQTALA. The mixture of protein and beads was stirred at room temperature for 3 hours in 10 mM MES, pH 5.0, containing 4 M urea. The supernatant was removed from the beads and analyzed using SDS-PAGE and silver stain. FIG. 7 shows a silver stained gel providing the results of a peptide competition experiment. Lane 1 provides molecular weight markers. Lane 2 shows that non-imprinted control beads capture no estrogen receptor (ER) protein from solution. Lane 3 shows that ER imprinted beads capture and thus sequester estrogen receptor from solution. Lanes 4 and 5 demonstrate that excess ER peptide, SQN-PQSQ compete with full length estrogen receptor for capture by the ER imprinted beads, thus decreasing the amount estrogen receptor sequestered from solution. Lane 4 has a 100-fold excess of the ER peptide relative to estrogen receptor. Lane 5 has a 500-fold excess of ER peptide. Lanes 6 and 7 demonstrate that a seven amino acid peptide, STQTALA, that is unrelated to estrogen receptor fails to compete with estrogen receptor for binding sites on the ER imprinted beads. Thus the ER imprinted beads selectively capture estrogen receptor. Lane 6 has a 100-fold excess of peptide STQTALA. Lane 7 has a 500-fold excess of peptide STQTALA.

The specificity of binding is demonstrated by the fact that estrogen receptor binding was competed to background levels by increasing concentrations of the peptide SQN-PQSQ (lanes 4 (100-fold excess) and 5 (500-fold excess). The presence of an unrelated seven amino acid, STQTALA, failed to affect the capture of estrogen receptor by ER imprinted beads (Lanes 6 and 7). This demonstrates that binding is occurring at the imprint cavity and not through other nonspecific mechanisms.

To demonstrate that the ER imprinted beads were capable of specifically binding estrogen receptor in a complex mixture, the beads of Example 8 were incubated at room temperature with a cell lysate spiked with 1% estrogen receptor in 10 mM MES, pH 5.0, containing 4 M urea. The imprint beads were separated from the supernatant. The protein bound to the imprint beads was eluted with a sample buffer (125 mM Tris-HCl, pH 6.8, 5% v:v 2-mercaptoethanol, 10% v:v glycerol, 2.5% w:v SDS, 0.05% w:v bromophenol blue). The eluted proteins were analyzed using SDS-PAGE and silver stain. FIG. 8 shows a silver stained gel. Lane 1 is the estrogen receptor spiked cell lysate. Lane 2 is the supernatant containing protein not captured by the beads. Lane 3 is the protein eluted from the ER imprinted beads. The elution appeared as a smear on the gel.

A western blot was performed to confirm the identity of the protein captured from the cell lysate. The probing antibody was murine IgM specific for recombinant human ESRII (Sigma, E1276, clone 9.88). The second antibody was goat anti-murine IgM antibody conjugated to horseradish peroxidase (Pierce, CN/DAB kit, Catalog No. 34000).

FIG. 9 shows the resulting western blot. Lane 1 is recombinant estrogen receptor. Lane 2 is the cell lysate spiked with estrogen receptor. Lane 3 is the cell lysate alone. Lane 4 is the protein eluted from non-imprinted control beads after being exposed to recombinant estrogen receptor alone. Lane 5 is the protein eluted from non-imprinted control beads exposed to cell lysate spiked with estrogen receptor. Lane 6 is the protein eluted from non-imprinted control beads exposed to cell lysate alone. Lane 7 is the protein eluted from ER imprinted beads exposed to recombinant estrogen receptor alone. Lane 8 is the protein eluted from ER imprinted beads exposed to cell lysate spiked with estrogen receptor. Lane 9 is the protein eluted from ER imprinted beads exposed to cell lysate alone. The double band in Lane 8 shows that the ER imprinted beads specifically capture both the recombinant estrogen receptor used to spike the cell lysate as well as the estrogen receptor beta expressed in the human cell line T47D used to create the lysate. The strong bands in lanes 1–3 are the heavy and light chains of the antibody used for immunoprecipitation.

6.10 Example 10

Shear Intensity Prior to Polymerization Dictate Ultimate Particle Size

In this example, we demonstrate the effect of the intensity of shearing forces on particle size.

The acrylamide beads were prepared in an inverse emulsion system. The nonionic surfactant Arlacel 83 was used to generate the inverse emulsion. The aqueous phase of the inverse emulsion was prepared by dissolving 1 g acrylamide and 0.17 g N-N'-ethylene bisacrylamide in 5 ml of 4 M urea and 10 mM MES pH 6.0. The organic phase of the inverse emulsion was prepared by dissolving 1.95 g Arlacel 83 (Uniqema) and 15 mg 2,2'-azobisisobutyronitrile in 27.6 g Isopar M (Exxon). The aqueous (5 ml) and organic phases (5 g) were mixed and purged with nitrogen for 10 min at 15° C. The inverse emulsion was prepared by four different methods. In one case, the aqueous and organic phases were stirred together. In a second experiment the aqueous and organic phases were vortexed at maximum speed for one minute. In the third experiment, the aqueous and organic phases were stirred and then forced 5 times through a 10 ml syringe with a 21-guage 6Δ-long needle. In the final experiment, the aqueous and organic phases were sonicated with a Virtis Virsonic 60 sonicator at 50% power for 30 seconds.

Polymerization was initiated with ultraviolet light at 365 nm and proceeded at 15° C. for 12 hr under continuous nitrogen flow. A latex comprising water-swollen polymeric beads dispersed in Isopar M was obtained.

The size of the resulting particles is a function of the highest intensity of shear to which the mixture was exposed prior to initiating polymerization. FIG. 10A beads formed by stirring together the aqueous and organic phases. FIG. 10B shows that vortexing the solution significantly decreases the size of each isolated bead of the discontinuous aqueous phase. FIG. 10C demonstrates the decrease in size caused by syringe homogenizing the solution prior to polymerization. Finally, as shown in FIG. 10D sonication of the solution prior to polymerization produces the smallest aqueous phase beads.

6.11 Example 11

Polymerization does not Affect Size of Aqueous Particles in Inverse Emulsion In this example, we demonstrate that the size of the droplets of the noncontinuous phase of the inverse emulsion does not change during polymerization.

The acrylamide beads were prepared in an inverse emulsion system. The nonionic surfactant Arlacel 83 was used to generate the inverse emulsion. The aqueous phase of the inverse emulsion was prepared by dissolving 1 g acrylamide and 0.17 g N-N'-ethylene bisacrylamide in 5 ml of 4 M urea and 10 mM MES pH 6.0. The organic phase of the inverse emulsion was prepared by dissolving 1.95 g Arlacel 83 (Uniqema) and 15 mg 2,2'-azobisisobutyronitrile in 27.6 g Isopar M (Exxon). The aqueous (5 ml) and organic phases (5 g) were mixed and purged with nitrogen for 10 min at 15° C. The inverse emulsion was prepared by vortexing as in Example 10, above. FIG. 11A is a photograph of the inverse emulsion immediately after the inverse emulsion was formed.

Polymerization was initiated with ultraviolet light at 365 nm and proceeded at 15° C. for 12 hr under continuous nitrogen flow. A latex comprising water-swollen polymeric beads dispersed in Isopar M was obtained. FIG. 11B is a photograph of the resulting polymeric beads.

The present invention is not to be limited in scope by the exemplified embodiments, which are intended as illustrations of single aspects of the invention, and any compositions and methods which are functionally equivalent are within the scope of the invention. Indeed, various modifications of the invention in addition to those described above will become apparent to those skilled in the art from the foregoing description and accompanying drawings. Such modifications are intended to fall within the scope of the appended claims.

All references cited herein are hereby incorporated by reference in their entirety.

---

What is claimed is:

1. A method of making an imprint bead comprising the steps of:
    emulsifying a composition comprising a polar solvent, a non-polar solvent, an organic monomer which is polymerizable in aqueous solution and a conjugate molecule, said conjugate molecule comprising a template moiety and a tail moiety, to form an inverse emulsion, wherein the template moiety is capable of partitioning into a noncontinuous phase of the inverse emulsion and the tail moiety is capable of partitioning into a continuous phase of the inverse emulsion;
    polymerizing the organic monomer; and
    removing the conjugate molecule.

2. The method of claim 1 wherein the polar solvent is water.

3. The method of claim 1 wherein the composition further comprises a surfactant.

4. The method of claim 3 wherein the surfactant is a nonionic surfactant.

5. The method of claim 4 wherein the nonionic surfactant is selected from the group consisting of sorbitan oleates, block copolymers, and glycerol esters.

6. The method of claim 3, wherein the surfactant have a hydrophilic/lipophilic balance (HLB) value of between about 3 and about 6.

7. The method of claim 1 wherein the composition further comprises a dispersant.

8. The method of claim 6 wherein the dispersant comprises polyisobutylene.

9. The method of claim 7, wherein the dispersant have a hydrophilic/lipophilic balance (HLB) value of between about 3 and about 6.

10. The method of claim 1 wherein the organic monomer is selected from the group consisting of styrene, methyl methacrylate, 2-hydroxyethyl methacrylate, 2-hydroxyethyl acrylate, methyl acrylate, acrylamide, vinyl ether, vinyl acetate, divinylbenzene, ethylene glycol dimethacrylate, ethylene glycol diacrylate, pentaerythritol dimethacrylate, pentaerythritol diacrylate, N,N'-methylenebisacrylamide, N,N'-ethylenebisacrylamide, N,N'-(1,2-dihydroxyethylene) bis-acrylamide, trimethylolpropane trimethacrylate and vinyl cyclodextrin.

11. The method of claim 1 wherein the composition further comprises a cross-linking agent.

12. The method of claim 1 in which the template moiety and the tail moiety are attached to one another via a linker.

13. The method of claim 1 wherein the tail moiety comprises a lipid or fatty acid.

14. The method of claim 1, wherein the template moiety corresponds to a portion of a macromolecule of interest.

15. The method of claim 14, wherein the template moiety corresponds to a terminal portion of the macromolecule.

16. The method of claim 14, wherein the macromolecule is a polynucleotide and the template moiety is an oligonucleotide.

17. The method of claim 14, wherein the macromolecule is a glycoprotein or polysaccharide and the template moiety is an oligosaccharide.

18. The method of claim 14, wherein the macromolecule is a polypeptide and the template moiety is a peptide.

19. The method of claim 18, wherein the sequence of the peptide corresponds to a contiguous sequence of the polypeptide.

20. The method of claim 19, wherein the peptide is between 3 and 15 amino acids in length.

21. The method of claim 20, wherein the peptide is between 4 and 15 amino acids in length.

22. The method of claim 21, wherein the peptide is between 4 and 7 amino acids in length.

23. The method of claim 18, wherein the portion of the polypeptide comprises the C-terminus of the polypeptide.

24. A collection of imprint beads made by the process comprising:

emulsifying a composition comprising a polar solvent, a non-polar solvent, an organic monomer which is polymerizable in aqueous solution and a conjugate molecule, said conjugate molecule comprising a template moiety and a tail moiety, to form an inverse emulsion, wherein the template moiety is capable of partitioning into a noncontinuous phase of the inverse emulsion and the tail moiety is capable of partitioning into a continuous phase of the inverse emulsion;

polymerizing the organic monomer; and removing the conjugate molecule.

* * * * *

UNITED STATES PATENT AND TRADEMARK OFFICE
CERTIFICATE OF CORRECTION

PATENT NO. : 7,105,289 B2
APPLICATION NO. : 10/121331
DATED : September 12, 2006
INVENTOR(S) : Huang et al.

It is certified that error appears in the above-identified patent and that said Letters Patent is hereby corrected as shown below:

Column 12, Line 60: After "correspond", insert --to--

Column 15, Line 1: Delete "does"

Column 16, Line 50: After "moiety", insert --is--

Column 17, Line 56: Change "such (Eisenberg," to --(such as Eisenberg,--

Column 26, Line 63: Change "(lnigema)" to --(Uniquema)--

Column 27, Line 49: Insert a period after "receptor"

Column 27, Line 50: Before "estrogen", change "a" to --an--

Column 28, Line 18: After "excess)", insert -- ) --

Column 29, Line 24: Change "6Δ-long" to --6"-long--

Column 31, Claim 8, Line 59: Change "6" to --7--

Signed and Sealed this

Sixteenth Day of January, 2007

JON W. DUDAS
*Director of the United States Patent and Trademark Office*